United States Patent
Van Acker et al.

(10) Patent No.: US 7,129,036 B1
(45) Date of Patent: Oct. 31, 2006

(54) REPORTER MOLECULES AND METHODS FOR ASSAYING THE LIPIDATIONS STATUS OF A CELL

(75) Inventors: Koenraad Lodewijk August Van Acker, Temse (BE); Inge Dierynck, Wilrijk (BE); Rudi Wilfried Jan Pauwels, Bonheiden (BE)

(73) Assignee: Tibotec BVBA (BE)

( * ) Notice: Subject to any disclaimer, the term of this patent is extended or adjusted under 35 U.S.C. 154(b) by 0 days.

(21) Appl. No.: 09/979,170

(22) PCT Filed: May 26, 2000

(86) PCT No.: PCT/EP00/04919

§ 371 (c)(1),
(2), (4) Date: Mar. 4, 2002

(87) PCT Pub. No.: WO00/73497

PCT Pub. Date: Dec. 1, 2000

(30) Foreign Application Priority Data

May 26, 1999 (EP) .................................. 99201659

(51) Int. Cl.
*C12Q 1/00* (2006.01)
(52) U.S. Cl. ........................................ 435/4; 435/320.1
(58) Field of Classification Search ..................... 435/4
See application file for complete search history.

(56) References Cited

FOREIGN PATENT DOCUMENTS

| WO | WO94/13818 | 6/1994 |
|----|-----------|--------|
| WO | WO96/23898 | 8/1996 |
| WO | WO97/27212 | 7/1997 |
| WO | WO 97/27212 A1 | 7/1997 |
| WO | WO98/45704 | 10/1998 |
| WO | WO99/18856 | 4/1999 |

OTHER PUBLICATIONS

Liu et al (J of Cell Biology, 1997, 137:1525-1535).*
Ausubel et al (Short Protocols in Molecular Biology, 3rd ed. 1997, Unit 9).*
Google web definition, p. 1.*
Gura (Science, 1997, 278:1041-1042).*
Jain (Sci. Am., 1994, 271:58-65).*
Curti (Crit. Rev. in Oncology/Hematology, 1993, 14:29-39).*
Freshney (Culture of Animal Cells, A Manual of Basic Technique, Alan R. Liss, Inc., 1983, New York, p. 4).*
Dermer (Bio/Technology, 1994, 12:320).*

(Continued)

*Primary Examiner*—Jeffrey Siew
*Assistant Examiner*—Laura B. Goddard
(74) *Attorney, Agent, or Firm*—Yunling Ren

(57) ABSTRACT

The invention relates to reporter molecules comprising at least one detection domain capable of emitting a signal and at least one membrane anchoring domain, which promotes the association of the reporter molecule with a membrane. The degree and rate of membrane association of the reporter molecule is approximated by the signal emitted by the detection domain. This signal provides a marker for the membrane association status of the membrane anchoring portion, or of the reporter molecule as a whole. Treatments or agents may be tested for their ability to alter membrane association or localization by observing or measuring the signal emitted by the detection domain. Thus, the invention provides means and methods for determining the capability of an agent to interfere at least in part with the distribution of a reporter molecule in a cell. These methods are useful for drug discovery; the phenotypic evaluation of cells, preferably patient cells; and for tailoring a therapeutic program for treating a patient.

6 Claims, 8 Drawing Sheets

OTHER PUBLICATIONS

Norio Sakai et al., "Direct Visualization of the Translocation of the Y-Subspecies of Protein Kinase C in living Cells Using Fusion Proteins with Green Flourescent Protein", The Journal of Cell Biology, vol. 139, pp. 1465-1476, (1997).

Reinhold Welker et al., "Virion Incorporation of Human Immunodeficiency Virus Type 1 Nef is Metiated by a Bipartite Membrane-Targeting Signal: Analysis of Its Role in Enhancement of Viral Infectivity", Journal of Virocology, vol. 72, No. 11, pp. 8833-8840 (1998).

Feruccio Galbiati et al., "The Dually Acylated $NH_2$—terminal Domain of $G_{11\alpha}$ Is Sufficient to Target a Green Flourescent Protein Reporter to Cavelin-enriched Plasma Membrane Domains", The Journal of Biological Chemistry, vol. 274, No. 9, pp. 5843-5850 (1999).

Galbiati, F., et al., "The dually acylated $NH_2$—terminal domaining of $G_{i1\alpha}$ is sufficient to target a green flourescent protein reporter to cavelin-enriched plasma membrane domains," *J. Biol. Chem.*, 1999, *274(9)*, 5843-5850.

* cited by examiner

REPORTER MOLECULES AND METHODS FOR ASSAYING THE LIPIDATIONS STATUS OF A CELL

This application is a U.S. national phase application of PCT/EP00/04919, filed May 26, 2000. This application claims the benefit of priority of European Application EP99201659.2 filed May 26, 1999, now European Patent No. EP1185873 B1, issued Sep. 28, 2005, which is hereby incorporated by reference in its entirety.

The invention relates to reporter molecules capable of associating with artificial or cellular membranes. This invention further relates to reporter molecules that are also cleavable by high specificity proteases. In each embodiment, the reporter molecules of the invention are particularly useful for drug discovery and diagnostics.

Most proteinaceous molecules and other substances in a cell are not distributed in equal amounts throughout the cell. On the contrary, most substances and especially proteinaceous substances are effectively localized in certain parts of a cell. For instance, many proteins are effectively localized in or near the plasma membrane of a cell. For at least some of the localized proteinaceous molecules and other substances, the correct distribution in a cell is of crucial importance to the function of said molecule or said other substance in a cell.

Correct distribution of a proteinaceous molecule or an other substance in a cell may be insured in a number of different ways. One way to target a proteinaceous molecule to a particular location in a cell is through modifying said molecule during or after its synthesis. Modifications like glycosylation, phosphorylation, proteolytic cleavage etc., during or after protein synthesis have been studied extensively in the past. A more recently discovered enzyme-catalysed protein modification is the covalent attachment of lipid molecules. By this hydrophobic modification, predominantly hydrophilic proteins lacking membrane binding structures are converted to hydrophobic proteins and the binding of modified proteins to membranes (e.g. nuclear envelope, plasmamembrane) is promoted—thereby affecting the biological activity of the protein. (Schmidt. 1989).

For example, the saturated fatty acids, stearic, palmitic, and myristic acids, are mostly found to be attached to proteins in eukaryotic cells (McIlhinney. 1990). Each of these fatty acids labels different sub-populations of a limited number of cellular proteins (Sepp-Lorenzino et al. 1989, Maltese et al. 1987, Maltese. 1990). Myristic acid is normally attached to an N-terminal glycine of proteins via an amide bond during their synthesis (Wilcox et al. 1987). The attached myristic acid is stable and has a half life similar to that of the protein to which it is bound (McIlhinney. 1990). In palmitoylation, fatty acids are attached to proteins post-translationally via an alkali-labile ester linkage. This linkage is usually biological labile with a turnover faster than that of the protein (McIlhinney. 1990).

Prenylated proteins are modified by either a 15 carbon (C15) isoprenoid, farnesyl (F) or a 20 carbon (C20) isoprenoid, geranylgeranyl (GG). The C-terminal amino-acid sequence of the proteins to be modified serves to direct the addition of either of these isoprenoids (Maltese. 1990, Glomset et al. 1990). In this way, signalling molecules, including Ras and G proteins are targeted to the inner leaflet of the plasma membrane by a sequence of post translational modifications of the C-terminal CAAX motif [C=cysteine, A=aliphatic residue (val or ile), X=variable].

Recognition of minimum recognisable sequences, such as the CAAX motif, involve an obligatory covalent attachment of a lipid to the sulfhydryl group of cysteine (C) located four amino acids from the C-terminus (Casey et al. 1989, Reiss et al. 1990), followed by protease removal of the AAX tripeptides and methyl esterification of the resulting prenylated cysteine carboxyl terminus (Hancock et al. 1989). Proteins terminating with CAAX boxes, where X is leucine or isoleucine, are modified with the C20 geranylgeranyl pyrophosphate (GGPP) by the enzyme geranylgeranyltransferase I (GGTase I) (Yokoyama et al. 1991). In proteins were X is most often methionine (M), serine (S), cysteine (C), alanine (A) or glutamine (E), the C15 isoprenoid farnesyl is transferred from farnesyl pyrophosphate (FPP) by the enzyme farnesyltransferase (FTase) (Reiss et al. 1990, Reiss et al. 1991, Moores et al. 1991). Thus proteins containing C-terminal CAA (MSCAE) and CAAL are prenylated by Ftase and GGTase respectively (Clarke 1992, Schafer et al. 1992, Zhang et al. 1996).

Although FTase and GGTase I can bind both FPP and GGPP, only GGTase I is able to transfer both to protein substrates. In contrast, FTase can only farnesylate some GGTase I substrates (Armstrong et al. 1995). A third related prenyl transferase, GGTase II, does not recognise CAAX boxes but rather transfers GG from GGPP to proteins ending in XXCC or XCXC which are double geranylgeranylated (Seabra et al 1992, Khosravi-Far et al. 1992), X and C have the above mentioned meaning.

Involvement of Lipid-Directed Localization and Ras in Cancer

Cells respond to signals from extracellular stimuli via a complicated network of highly regulated events collectively referred to as signal transduction pathways. Stimulation of these pathways results in changes in transcriptional activity (Karin et al. 1995, Hill et al. 1995). Whereas normal cells respond appropriately to extracellular stimuli, many precancerous and cancerous cells have lost this ability and display aberrant signalling. Ras, a member of the large superfamily of GTP binding proteins (G-proteins), plays a central role as a molecular switch, interfacing between extracellular receptors and intracellular effector proteins which in turn regulate growth regulatory pathways (Lowy et al, 1993). One of these effectors is a serine/threonine kinase, Raf (Pronk et al. 1994), which phosphorylates mitogen-activated protein kinase (MAPK).

Ras is active when bound to GTP and inactive when bound to GDP. Cycling from active to inactive is accomplished by the intrinsic GTPase activity of the protein. Some mutations in Ras abolish the GTPase activity and result in constitutively active forms of the protein. Thus, Ras proteins that are stuck in the active GTP-bound state, constitutively transmit growth signals and display their oncogenic activity (Lowy et al. 1993, Koshravi-Far et al. 1994). However, oncogenic activity can also result from overexpression of normal Ras proteins (Barbacid. 1987).

There are three mammalian Ras genes that encode four highly homologous 21 kDa proteins: H-, N-, K(i4)A- and K(i4)B-Ras. K(i4)A- and K(i4)B-Ras are encoded by splice variants of the Ki-Ras gene (Barbacid. 1987, Lowy et al. 1993). Oncogenic mutations in Ras genes, especially Ki4B-Ras and N-Ras, contribute to the formation of 30% of various human malignancies. Mutant ras genes were found in 50% of colorectal, 90% of pancreas and 20% of lung cancers. Thus, disrupting the Ras signalling pathway could have significant potential as a cancer chemopreventive strategy (Bos 1988, Bos 1989, Barbacid 1987).

Many approaches have been considered to inhibit the oncogenic function of Ras but the greatest progress towards developing novel chemotherapeutics against Ras induced cell transformation has centred on inhibiting the enzyme FTase. This strategy is based on the observation that the four Ras proteins, synthesised as biologically inactive cytosolic proteins, require post translational modification with a farnesyl moiety for oncogenic activity. Indeed, it has been known for some time that association of Ras to the inner leaflet of the plasma membrane is required for its transforming activity (Willumsen et al. 1984). However, it was not until the biochemistry of Ras post-translational modifications leading to membrane association (Casey et al. 1989, Hancock et al. 1989, Schafer et al. 1989) was unravelled that potential anti-neoplastic (anticancer) drug targets began to be identified.

Additional lipid modifications of cysteines upstream of CAAX with a palmitoyl group further stabilize the association of H-, N- and KiA-Ras proteins with the plasma membrane (Hancock et al 1990). KiB-Ras, on the other hand, is not palmitoylated, but contains a polylysine stretch upstream of the farnesylated cysteine, which is believed to further stabilize the interaction of the protein with the plasma membrane (Hancock et al 1990). Although several steps are involved in targeting Ras to the plasmamembrane, farnesylation seems to be the only step that is required and sufficient for Ras transforming activity (Jackson et al 1990, Kato et al. 1992). Therefore, FTase has become one of the most sought-after targets for developing novel anti-cancer drugs. The therapeutic goal is to capitalise on this new information and translate it into novel biological and pharmacological agents that will demonstrate greater efficacy and lower toxicity than currently available cancer cytotoxic drugs (Gibbs et al. 1997).

Rational design of FTase inhibitors can be subdivided into three broad categories (Gibbs et al. 1997, Keloff et al. 1997)): (i) compounds competitive with the isoprenoid FPP, (ii) compounds competitive with the tetrapeptide CAAX and (iii) bisubstrate analogues that combine features of both the FPP and CAAX mimetics. The problem with (i) is that compounds competitive with respect to FPP need to overcome the high avidity of FTase for FPP. FTase binds FPP with low nanomolar affinity while cellular FPP concentrations are near micromolar. Thus, inhibitors of FTase require very tight Ki and would have to be very selective for FTase over other FPP utilising enzymes (e.g. squalene synthase). Problems with CAAX peptidomimetics (ii) are cellular protease-lability and impaired membrane permeability caused by C-terminal carboxylate. Various peptide bond modifications and prodrug design by temporary masking of the carboxylate charge proved to be sufficient to generate cell active drugs. However, many of these compounds still contained a thiol group which is subject to oxidation and is metabolically reactive. Bisubstrate inhibitors (iii) were deduced from enzymological studies of FTase which revealed a sequential mechanism. This raised the idea that compounds that mimic the transition state FTase-FPP-CAAX ternary complex would be potent FTase inhibitors. Potent bisubstrate inhibitors have been found but the large size of these molecules may compromise their pharmacological properties in vivo.

Other approaches for obtaining inhibitors of any enzyme relate to targeted random screens from either natural products (microorganisms, soils, plants etc.) or synthetic chemical libraries. Such screens present an immense pool of structures for random screening and present a powerful means to obtain chemical leads that can be modified by traditional medicinal chemistry for further development (Sebti et al. 1997). A number of FTase inhibitors were identified by a variety of random screens. For example, a class of novel nonpeptidic, nonsulfhydryl tricyclic FTase inhibitors that are competitive inhibitors with respect to FPP were found in a collection of antihistamines (Bishop et al. 1995). However, these compounds exhibit rather low potency compared to CAAX mimetics which makes them not suitable for evaluation in vivo (Gibbs et al. 1994). More recently, a promising new class of competitive FTase inhibitors has been discovered in the course of other FPP-mimic enzyme (squalene synthase) inhibitors (Aoyama et al. 1998). The activity of chemically optimized analogues compares with CAAX mimic FTase inhibitors.

In cells, FPTase inhibitors block cellular farnesylation. In these studies farnesylation and geranylgeranylation of proteins is examined by incubation of cell cultures with the FPP precursor [3H]mevalonate (Hancock et al. 1989, Kohl et al. 1993, James et al. 1993). Nevertheless, in cellular assays the concentration of FTase inhibitors necessary to achieve their action is often 1000 times greater than the IC50 for inhibition of FTase in vitro, indicating severe limitations to cell activity. The inhibition of Ras mediated cellular effects by FTase inhibitors has similarly been demonstrated in cell culture assays that monitor key phenotypes of cellular transformation: anchorage dependent (plastic, Kohl et al. 1993, James et al. 1993)—and independent (soft agar, Kohl et al. 1993) growth, the rapidity of growth in monolayer (James et al. 1993), morphological transformation and alterations in the cytoskeleton (Prendergast et al. 1994).

The biochemical specificity of FTase inhibitors is unquestioned, since these agents do not block geranylgeranylation of proteins (Gibbs et al. 1993, Kohl et al. 1993, James et al. 1993, Bishop et al. 1995, Cox et al. 1994). However, it is important to note that the Ras mutation status of human tumours has been reported not to correlate with their sensitivity to FTase inhibitors. Moreover, it is incorrect to refer to FTase inhibitors as specific Ras inhibitors since FTase inhibitors target at least 18 farnesylated proteins of which some are important for malignant transformation (James et al. 1994). One example is the suppression of src transformation by FTase inhibitors (James et al. 1993). The biochemical mechanism by which FTase inhibitors lead to tumour inhibition is thus an important issue. The ability of FTase inhibitors to block the Ras dependent constitutive activation MAPK cascade is now well established (Cox et al. 1994, James et al. 1994).

Nonfarnesylated oncogenic Ha-Ras can exhibit a dominant negative effect and can inhibit the function of membrane bound Ras in some circumstances (Stacey et al. 1991). FTase inhibitors can induce accumulation of cytosolic complexes of GTP locked Ras with its effectors, such as Raf (Lerner et al. 1995, Miyake et al. 1996). This eventually leads to sequestration of Ras effector targets. Thus, in tumours were Ras is GTP locked, cytosolic Ras can accumulate as a dominant negative protein that will further inhibit tumour growth. Since wild type FTase inhibitor mediated cytosolic Ras does not sequester its effectors and hence, does not display the dominant negative phenotype, the observed inhibition would be selective for tumour cells. Moreover, several studies reported that concentrations of FTase inhibitors such as BZA-5B and FTI-277, required to block the activities of enzymes in the MAP kinase pathway, were lower than those necessary to completely inhibit Ras processing. This also suggests that nonfarnesylated activated H-Ras is a dominant inhibitor of the action of farnesylated activated H-Ras in the FTase inhibitor treated cells. Thus, a partial inhibition of Ras processing could result in a selective inhibition of oncogenic, but not normal signalling (James et al. 1994, Lerner et al. 1995).

One drawback of studies using ras oncogene-transformed cells to investigate the mechanism of action of FTase inhibitors is that H-Ras was used and it was soon discovered that the most prevalent K-Ras was considerably resistant to FTase inhibitors (James et al. 1994, Lerner et al. 1995). Much higher concentrations of inhibitor are required to inhibit KB-Ras than H-Ras. An attractive mechanism for this resistance is that KB-Ras is processed by GGTase-1 when FTase is blocked (Lerner et al 1995, Whyte et al. 1997, Rowell et al. 1997). In vitro, KB-Ras is a substrate for GGTase-I (James et al. 1995b). GGTase-1 inhibitors block the KB-Ras processing in KB-Ras transformed cells providing pharmacological evidence that cross prenylation may be occurring in cells (Lerner et al. 1995b). These observations underscore the necessity of using KB-Ras transformed cells for testing potential inhibitors in vitro and in vivo.

Very recently, it was shown that coexposure of FTase and GGTase-I inhibitors in human tumours are required for inhibition of oncogenic KB-Ras prenylation while each inhibitor alone is sufficient to suppress human tumour growth in nude mouse xenografts (Sun et al 1998). The fact that GGTase-I inhibitors have anti-tumour activity of their own suggests that some substrates for GGTase I are important for malignant transformation (Sun et al. 1998). Also, FTase inhibitors, which are not able to inhibit KB-Ras processing, are efficacious in inhibiting tumour growth suggesting that there exist other farnesylated proteins other than Ras important for malignant transformation (Sun et al. 1998).

In a second in vivo model an FTase inhibitor induced a dramatic regression of mammary and salivary carcinomas in a viral Ha-Ras oncomouse model (Kohl et al. 1996). In these transgenic mice, the FTase inhibitors are administered to pre-existing tumours, in contrast to nude mouse tumour models. Chronic administration of the inhibitor was required as tumours reappeared upon cessation of treatment (Kohl et al. 1996). In both the nude mouse and oncomouse models, efficacy was achieved in the absence of gross microscopic toxicity, suggesting that such FTase inhibitors might be effective and safe agents for the treatment of human cancers (Omer et al. 1997). So far, toxicity has not been reported in mice treated with any of the FTase inhibitors tested. This observation is in sharp contrast to findings with previously developed chemotherapeutic agents, which often must be used at their maximally tolerated dose to obtain antitumour activity (Gibbs et al. 1997).

Although the biological results seen with FTase inhibitors are widely accepted, the precise reasons for the lack of toxicity towards normal cells in culture as well as animal studies have not been established. For instance, the growth of Ras-transformed culture cells is much more sensitive to FTase inhibitors as compared to their normal parental cells. Given that Ras function appears to be essential for all cells, it is somewhat unexpected that normal cells should be relatively insensitive to FTase inhibitors. Gibbs et al. (1997) have suggested a number of possible explanations for these effects have been suggested: (i) Functionally redundant growth factor networks in normal cells that allow them to tolerate the downregulation of Ras function. In other words, proliferation of normal cells is dependent on more than one growth factor, and one growth factor activates multiple intracellular signalling pathways (Keloff et al. 1997). (ii) In the case of KB-Ras, geranylgeranylation rather than farnesylation could take place and wild type KB-Ras may also provide critical biological functions. However, cross prenylation (geranylgeranylation) of unmutated Ras in the absence of functional FTase is not a satisfactory explanation as it then calls into question why cells with mutated N or Ki-Ras are sensitive to FTase inhibitors (Omer et al. 1997, Gibbs et al. 1997). (iii) Not all farnesylated proteins have the same degree of FTase inhibition in cells. Thus, selective inhibition of H- versus KB-Ras mediated signalling may allow continued growth of normal cells (James et al. 1995b). (iiii) in accord with (iii), the function of farnesylated proteins involved in cellular transformation may be more sensitive to the action of an FTase inhibitor than are the functions of those same proteins in normal cells. Hence, the quantitative relationship between a specific protein's function and its degree of farnesylation may vary, which in turn determines the degree of inhibition of farnesylation that is required to block the biological function.

Human cancers having mutated Ras typically have other genetic alterations such as loss of tumour suppressors (Gibbs et al. 1996). A critical question has been whether compromising Ras function in a complex genetic background will yield an anti-tumour effect. Work of Shirasawa et al. (1993) has provided evidence that Ras maintains a critical function in tumour cells that have mutations in other oncogenes or tumour suppressor genes. Specifically, Shirasawa genetically disrupted the mutated KB-Ras gene in several human colon cell lines known to have other mutations and observed that the cells were no longer tumorigenic in a nude mouse tumour explant model (Shirasawa et al. 1993).

The fact that GGTase I inhibitors also inhibit human tumour growth, albeit with less efficacy than FTase inhibitors suggest that besides farnesylated proteins, geranylgeranylated proteins also play an important role in malignant transformation.

The biological effects of FTase inhibitors suggest that they are not properly considered specific inhibitors of Ras. (Gibbs et al. 1997). Nevertheless, FTase inhibitors have demonstrated a remarkable therapeutic index in cell culture and in mice (Gibbs et al. 1994, Kohl et al. 1994). Finally, an important clinical issue is if administration of FTase inhibitors will lead to drug resistance. FTase inhibitor resistance has been observed, both in cell culture and in animals (Kohl et al. 1995, Prendergast et al. 1996). Thus the ultimate arbiter of FTase utility will be when compounds with adequate pharmacological profiles are tested in the clinic (Omer et al. 1997).

Anti-Cancer Agents and Apoptosis

Apoptosis or programmed cell death serves as a major mechanism for the precise regulation of cell numbers, and as a defence mechanism to remove unwanted and potentially dangerous cells, such as virus-infected cells or cells with DNA damage or growth dysregulation that could become precursors of tumour cells. Hence, defects in the activation or execution of the apoptotic pathway can lead to the development of oncogenesis. An important event in the progression of many malignancies is the loss of function of the p53 tumour suppressor gene. The p53 protein, a nuclear DNA-binding protein, is involved in the induction of apoptosis triggered by DNA damage and inappropriate oncogene activation. It is a transcriptional activator of a specific set of target genes, including the cell growth inhibitors p21WAF1 and Gadd45, and interacts directly with many cellular proteins (Wang and Harris 1997). The p53 gene is frequently mutated in the majority of human malignancies, suggesting the importance of p53-dependent apoptosis in the control of cancer growth (Bellamy 1996).

It has recently become widely accepted that cell killing induced by anticancer agents is the result of programmed cell death (Weinberg 1996). The p53 tumour suppressor protein, in particular, appears to be intimately linked to the activation of an apoptotic pathway in response to treatment with radiation or chemotherapy. It seems that drugs with different modes of action initiate responses which engage apoptosis (Smets 1994). Antimetabolites like purine and cytidine analogues, and topoisomerase inhibitors trigger the induction of cell death by interference with the DNA replication and inhibition. Distinct from the DNA-damaging agents, the taxoid drugs, which target the stabilisation of the microtubuli system, commit cells to apoptosis via p53-independent pathways. The insight into the mechanism of action of current anti-cancer chemotherapy has lead to a search for apoptosis-inducing agents, either via p53 or other regulatory proteins.

Apoptosis is regulated by a series of events leading to stereotypic biochemical and morphological changes including membrane blebbing, cell shrinkage, chromatin condensation, DNA cleavage and fragmentation of the cell into membrane-bound apoptotic bodies. The central event in the apoptotic pathway is the activation of a hierarchy of interleukin-1B (1L-1B) converting enzyme (ICE)-like proteases or caspases, a family of cysteine proteases with an absolute requirement for cleavage after an aspartic acid residue (for a reviews see Cohen 1997, Thornberry and Lazebnek 1998). These high specificity proteases are synthesized as inactive proenzymes and are converted to active enzymes by cleavage at specific Asp residues followed by association of a large and a small subunit to form a heterodimer.

Caspases are close homologues of the *Caenorhabditis elegans* ced-3 gene product shown to be essential for apoptosis during nematodal development (Shaham and Horvitz 1996). They mediate the proteolysis of a discrete number of specific proteins leading to an irreversible commitment of cells to undergo apoptosis. Caspase-dependent cleavage inactivates proteins involved in repair mechanisms of the cell cycle (including the nuclear proteins, poly ADP-ribose polymerase (PARP) and DNA dependent-kinase), leads to degradation of structural proteins such as lamins, or activate proteins to become proapoptotic (p21-activated kinase and the caspases themselves). Also the signal transduction proteins MEKK1, p21-activated kinase 2, the focal adhesion kinase, RAS-GTPase activating protein, and Raf-1 were shown to be caspase substrates (idmann et al. 1998). The essential role of caspase activity in the execution phase of the apoptotic process is illustrated by the fact that inhibition of caspases generally leads to inhibition of apoptosis. However, different caspases contribute differentially to the apoptotic program in different cell types.

The caspases target proteins for cleavage based on the presence of a tetrapeptide recognition motif—a minimal sequence necessary for proteolysis. The sequence of this motif differs significantly among caspases, and some proteins that contain the optimal tetrapeptide sequence are not efficiently cleaved, implying that tertiairy structural elements may influence substrate recognition (Thornberry 1997). Nevertheless, any difficulties with proteolysis of a particular peptide may be overcome by adding additional amino acids sequence corresponding to the target sequence flanking the tetrapeptide.

The fourteen mammalian caspases identified to date can be classified as initiating or upstream caspases (e.g. caspases-2, -8 and -10) or as effector or downstream caspases (e.g. caspase-3, -6 and -7), the latter being the key executioners of the apoptotic pathway. Specific peptide inhibitors of caspase-3 and -7 such as Z-DEVD-fluoromethylketone interfere with most forms of mammalian apoptosis (Gurtu et al. 1997). Tumour necrosis factor, FAS ligand and chemotherapeutic drugs are able to induce apoptosis by activation of caspase-3 (Nagata 1997), which is responsible either wholly or in part for the proteolysis of a large number of substrates, including PARP. Caspase-3 recognizes a Asp-Xaa-Xaa-Asp (DXXD)-like motif (DEVD in PARP and DNA dependent-kinase), with a requirement for an Asp in the P1-position and a marked preference for an Asp in the P4 position. Caspase 1, in contrast cleaves at the naturally-occurring sequence: Y-V-H-D-*-A, where "*" marks the site of cleavage.

SUMMARY OF THE INVENTION

The present invention relates to two principal embodiments of novel reporter molecules. The first embodiment relates to a reporter molecule comprising at least one detection domain capable of emitting a signal and at least one anchoring domain. The membrane anchoring domain directly or indirectly promotes the association of the reporter molecule with a subcellular compartment, or preferably with a membrane. The degree and rate of membrane association of the reporter molecule may be monitored or assayed by analyzing the signal emitted by the detection domain. This signal provides a marker for the membrane association status of the membrane anchoring portion, or of the reporter molecule as a whole. Thus, treatments or agents may be tested for their ability to alter membrane association or localization by observing or measuring the signal emitted by the detection domain. For example, the reporter molecules of the first embodiment are particularly useful for assaying for a compound that alters lipidation by:

A) providing a membrane;

B) providing a reporter molecule comprising at least one detection domain capable of emitting fluorescent, luminescent, radioactive, or chromatic signal, or capable of absorbing a resonance energy which is then transferred (emitted) to a second molecule that emits a detectable signal; and at least one membrane anchoring domain comprising sufficient amino acid sequence of a ras gene, or variant thereof, to promote farnesylation;

C) providing conditions which permit the reporter molecule to associate with the membrane;

D) providing conditions which permit the emission of a signal from the detection domain;

E) observing or measuring the signal emitted by the detection domain;

F) duplicating steps A) through E) in the presence of a compound to be tested;

G) comparing the signals emitted in the presence and absence of the compound tested to determine the effect of the compound on lipidation.

The reporter molecules of the first general embodiment are similarly useful for assessing the sensitivity of a cell to a chemotherapeutic agent by:

A) providing a reporter molecule comprising at least one detection domain capable of emitting fluorescent, luminescent, radioactive, or chromatic signal, or capable of absorbing a resonance energy which is then transferred (emitted) to a second molecule that emits a detectable signal; and at least one membrane anchoring domain comprising sufficient amino acid sequence to promote lipidation;

B) providing a cell to be tested;

C) providing conditions which permit the reporter molecule to associate with cellular membranes;

D) providing conditions which permit the emission of a signal from the detection domain;

E) observing or measuring the signal emitted by the detection domain;

F) duplicating steps A) through E) in the presence of the agent to be tested;

G) comparing the signals emitted in the presence and absence of the agent tested in order to assess the sensitivity of a cell to the chemotherapeutic agent or agents tested.

Moreover, where the cells assessed for sensitivity to a chemotherapeutic agent are malignant cells from a patient, the present invention further provides a method for selecting an appropriate anti-neoplastic therapy for treating that patient.

The second principal embodiment relates to a reporter molecule further comprising at least one high specificity protease recognition site. Proteolysis of the reporter molecule at a high specificity protease recognition site elicits or alters a signal from the detection domain.

Specifically, the reporter molecule comprises:

at least one detection domain capable of emitting a signal;

at least one high specificity protease recognition site;

at least one membrane anchoring domain, which promotes the association of the reporter molecule with a membrane or subcellular compartment; wherein proteolysis of the reporter molecule at said at least one high specificity protease recognition site elicits or alters a signal from the detection domain.

Throughout the second embodiment, it is understood that the membrane anchoring domain may be substituted with a subcellular anchoring domain, which promotes the association of the reporter molecule with a subcellular compartment. The subcellular compartment need not be membranous and, thus, includes the soluble portion of: the nucleus, cytosol, matrix and intermembrane spaces of mitochondria, vacuoles, lysosomes, golgi apparatus, peroxisomes, and other subcellular compartments. Nevertheless, cleavage of a high specificity protease recognition site alters the signal from the detection domain, preferably by releasing that portion of the reporter molecule from the anchoring domain, preferably by allowing the detection domain to diffuse throughout the cell, or to migrate to a different subcellular compartment.

The reporter molecule of the second embodiment provides a tool for a number of methods disclosed herein. Thus, the present invention further provides methods for assaying for high specificity proteases, methods for assaying for the effects of bioactive agents on proteolysis by high specific activity proteases, and methods for monitoring the biological effects of high specificity proteolysis, such as the tendency for a cell to undergo apoptosis.

In the context of the principal embodiments, it is an object of the invention to find an agent capable of redistributing a substance and/or a proteinaceous molecule in a cell. Such an agent may be capable of altering at least in part the function of said substance and/or proteinaceous molecule in said cell. Altering said function of said substance and/or proteinaceous molecule in said cell may lead to an at least in part altered phenotype of said cell. An agent capable of altering at least in part the phenotype a cell may be used for the development of medicaments for the treatment or the prevention of a disease. For instance, in a non-limiting example such as cancer, an agent capable of redistributing one or more proteinaceous molecules in cancer cells, is provided to said cells as a result of which the malignant phenotype of said cancer cells is at least in part decreased. The present invention provides one of ordinary skill with tools and methods to monitor the redistribution of proteinaceous molecule in a cell or among cellular compartments, thereby selecting efficacious agents for the treatment of cancers and other cellular abnormalities.

The ability to monitor the redistribution of a proteinaceous molecule in a cell may also be of importance for the development of treatments for other diseases such as infectious diseases or inherited diseases. A non-limiting example of such an inherited disease is Cystic Fibrosis, where a frequently occurring mutation of the CFTR protein appears to have a distribution defect. Normal CFTR is transported to the plasma membrane of a cell where it can exert its function as an ion channel. Said frequently occurring mutated CFTR does not appear to localise correctly to the plasma membrane. The means and methods of the invention may therefore also be used to select agents with the capacity to alter the distribution of said mutated CFTR into a suitable plasma membrane distribution in order to develop medicaments for the treatment of Cystic Fibrosis.

In one aspect the invention utilises a proteinaceous molecule comprising a localization part or domain, wherein said localization domain causes a certain distribution of said proteinaceous molecule in a cell, for the determination whether an agent provided to said cell is capable of altering the distribution of said proteinaceous molecule in said cell.

It is an object of the invention to find an agent capable of at least in part interfering with and/or at least in part changing the distribution of said proteinaceous molecule in a cell. Preferably, said agent is capable of changing the function of said proteinaceous molecule in said cell.

A further object of the present invention is to develop assays for finding agents that interfere at least in part or change at least in part the distribution of a proteinaceous molecule in a cell and thereby at least preselect agents with potential efficacy in altering the function of said molecule in a cell. Preferably said assays are suitable for the screening of a large number of different agents in preferably a high throughput setting.

It is a further object of the present invention to develop pharmaceuticals at least comprising one or more of said agents for treatment of disease.

It is also an object of the invention to develop assays for the phenotypic characterisation of a cell based on the capacity of an agent to redistribute at least in part a proteinaceous molecule in said cell.

DETAILED DESCRIPTION OF THE INVENTION

Figure 1A:
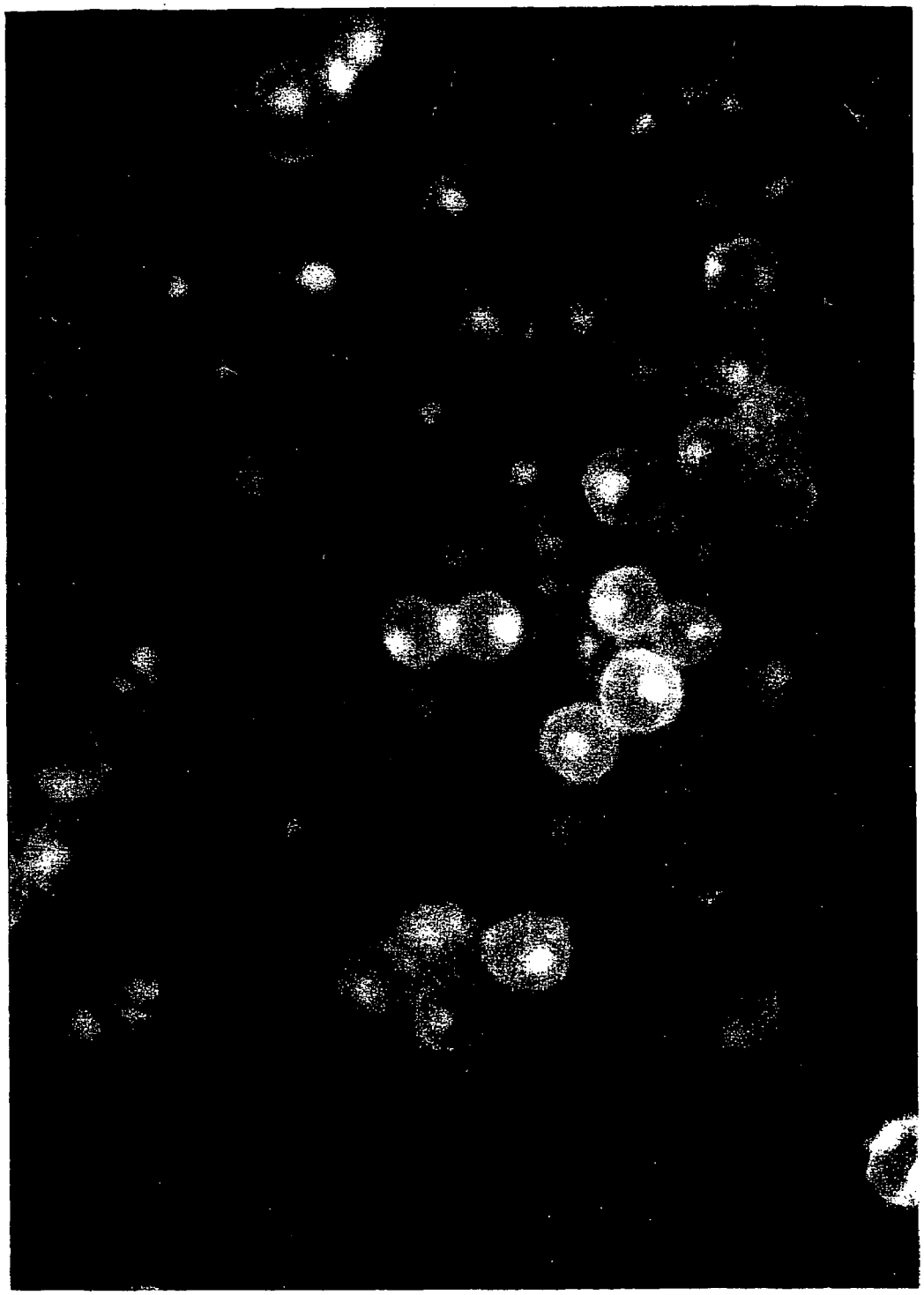
FIG. 1. K562 LNC-EGFP-RasF cells expressing membrane targeted EGFP at low (A, 240×) and high (B, 480×) magnification. Targeting of EGFP is evident by delineation of the membrane. Some cells exhibit eccentric bright spots which may be localized in the Golgi Apparatus.

The present invention relates to reporter molecules comprising at least one detection domain capable of emitting a signal and at least one membrane anchoring domain. The membrane anchoring domain directly or indirectly promotes the association of the reporter molecule with a membrane. The degree and rate of membrane association of the reporter molecule may be monitored or assayed by analyzing the signal emitted by the detection domain. In some embodiments, the reporter molecule further comprises at least one of high specificity protease recognition site. Proteolysis of the reporter molecule at high specificity protease recognition site elicits or alters a signal from the detection domain.

In one aspect the invention provides a method for determining the capability of an agent to interfere at least in part with the distribution of a substance in relation to one or membranes, or membrane compartments comprising:

A) providing a membrane;

B) providing a reporter molecule comprising a detection part which can be detected, and at least one localization part capable of directly or indirectly promoting the association of the detection part with a membrane;

C) providing conditions which permit the reporter molecule to associate with the membrane;

D) providing conditions which permit the emission of a signal from the detection part;

E) observing or measuring the signal emitted by the detection part;

F) duplicating steps A) through E) in the presence of an agent to be tested;

G) comparing the signals emitted in the presence and absence of the compound tested.

In one embodiment, the reporter molecule, or its detection part, contains a multiplicity of detection domains, which may be the same or different, and may emit the same or different signals. In one embodiment, a signal emitted by a detection domain changes in response to an alteration (such as cleavage, phosphorylation, or ligand binding) in some part of the molecule. Said detection part, or domain, may be the same part as said localization domain or different. The function of a detection domain is to allow detection of the reporter molecule, in particular to visualize its distribution. In one embodiment of the invention said reporter molecule comprises said proteinaceous molecule or a functional part, derivative and/or analogue thereof. In a preferred embodiment said reporter molecule comprises a localization domain which is said proteinaceous molecule or a functional part, derivative and/or analogue thereof and a detection part.

In a further embodiment, a reporter molecule within the scope of the invention has a localized distribution in a cell before said cell is provided with an agent. However, reporter molecules with an essentially even distribution in a cell before said cell is provided with said agent can also be used for the invention, for instance for determining the capability of an agent to induce a localized distribution of a reporter molecule with an even distribution in a cell. Preferably a reporter molecule is localized in a membrane of a cell, most preferably the plasma membrane.

Within the scope of the invention an agent may be added to a cell to prevent or induce a separation of a part determining at least in part the distribution of a proteinaceous molecule in a cell, from other part(s) of said proteinaceous molecule thereby at least in part altering the distribution of said other part(s). In a preferred embodiment said prevention or induction of said separation alters at least in part a function of said cell. A preferred method for preventing or inducing a separation is preventing or inducting proteolytic cleavage, preferably of a specific short amino-acid sequence in said proteinaceous molecule. Preferably said proteolytic cleavage is a caspase cleavage. Most preferably, the proteolytic cleavage is mediated by a high-specificity protease.

In the practice of one embodiment of the invention, a reporter molecule comprises one or more amino acid sequences encoding a recognition sequence for a high specificity protease and, thus, acts as a target or substrate for the high specificity protease. Said recognition sequence may occur anywhere in the reporter, preferably within the detection domain or between the detection and membrane anchoring domains. Thus, the recognition sequence may comprise a separate stretch of amino acids or comprise a part of the anchoring or detection domains. Said recognition sequence may be a single high specificity cleavage site, or multiple sites for the same or different high specificity cleavages. Exemplary arrangements of redundant and nested cleavage sites are disclosed in Nicholson (1999).

In one embodiment, the detection domain is a fluorescent protein in which a short recognition sequence has been inserted. In another embodiment, amino acids of the fluorescent protein have been mutated to encode a high specificity protease recognition domain by site-directed mutagenesis. Although the juxtaposition of recognition and detection domains is unlikely to adversely affect their function, one of ordinary skill will recognize that some reporter molecules comprising a high specificity cleavage site within a detection domain may not be active. Nevertheless, the design and testing of appropriate constructs is well within the skill of the routineer, moreover, the reporter molecules described herein may be constructed using routine methods such as those described in Sambrook et al. (1989).

As used herein, a high specificity protease is a naturally-occurring or genetically altered protease which recognizes a higher-order (secondary, tertiary, or quaternary) protein structure or, more preferably, a limited sequence of linear amino acids. In a highly preferred embodiment, a high specificity protease recognizes and cleaves a polypeptide at one or a few discrete amino acid sequences. These amino acid sequences are sufficiently complex as to not occur frequently in nature, consequently, where the protease recognizes an amino acid sequence, the recognition sequence comprises at least three, and preferably, four or more amino acids. Thus, a high specificity protease cleaves no more than 1 out of 100, preferably, no more than 1 out of 500, more preferably, no more than 1 out of 1000, and still more preferably, no more than 1 out of 5000 randomly chosen naturally-occurring proteins in an organism. Most preferably, a high specificity protease cleaves fewer than 2, 3, 4, 5, 10, or 20 naturally-occurring proteins in an organism. Any known or suspected high specificity protease cleavage (recognition) site may be used in the practice of this invention. These sites may comprise naturally-occurring sequences or derived consensus sequences.

It is further noted that the precise cleavage site for a high specificity protease need not be determined for the practice of this invention. Indeed, as long as the amino acid sequence of the region cleaved is determined, that region, or a portion of that region can be incorporated into a reporter molecule within the scope of the invention. Conversely, it is also not necessary to know the identity of a high specificity protease other than its propensity for cleaving a protein who's sequence can be determined. If a target region can be defined, the activity of any high specificity protease can be detected or determined according to the present invention. Consequently, by comparing the activity of a high specificity protease in the presence and absence of an agent, defined herein, the effect of the agent on the protease may be assessed.

Recognition sites for mammalian and human proteases are preferred and include both soluble and membrane-associated proteases. In one embodiment, a generally soluble protease activity can become associated with a membrane as a recombinant fusion protein, by the introduction of a heterologous membrane anchor sequence.

In a preferred embodiment, the high specificity recognition site is cleaved by a protease involved in apoptosis, for example a caspase (E.g., caspase-1, caspase-2, caspase-3, caspase-4, caspase-5, caspase-6, caspase-7, caspase-8, caspase-9, caspase-10, caspase-11, caspase-12, caspase-13 (ERICE), caspase-14), or other members of the ICE-ced3 gene family (see Thornberry et al. 1997). For the purpose of this invention, the caspase activator, granzyme B, is also referred to herein as a caspase. Also preferred is a portion of the cytosolic domain of the beta amyloid precursor protein (APP) (Cescato et al. 2000), especially the region containing the caspase-like recognition consensus, (IVL)ExD, (Weidemann et al. 1999), and regions containing alpha, beta, or gamma secretase sites; sequences encoding the cleavage site of carboxypeptidase A1 (CPA) (Hamstra et al. 1999), further preferred caspase target proteins are disclosed in Table 1 of Stroh and Schulz-Osthoff. (1998).

Naturally-occurring, and consensus cleavage sites for the caspases are well known in the art, and additional target sequences may be derived by positional scanning of combinatorial libraries (Thornberry et al., 1997) or, more traditionally, by sequencing the cleavage sites of naturally-occurring substrates. Representative cleavage sites and surrounding sequences are provided in Nicholson 1999; Stennicke and Salvesen 1999; Stroh and Schulze-Osthoff 1998; and PCT publication WO 99/18856. Exemplary substrates include WEHD (caspase-1), DEHD (caspase-2), W/LEGD caspase-4 and -5), VEHD (caspase-6), LETD (caspase-7), IETD (caspase-8), LEHD (caspase-9), (I/L/V/P)EHD (caspase-11) and IEPD (granzyme B).

Additional and non-limiting high specificity proteases for which recognition sites are known or sufficiently defined for the practice of this invention are defined in "Handbook of Proteolytic Enzymes," A. J. Barrett, N. D. Rawlings & J. F. Woessner Eds. (Academic Press, London 1998). Acceptable target recognition sites are also known for: Cathepsins such as: Cathepsin B, which are cysteine proteases implicated in cancer and having broad specificity characterized by a large hydrophobic amino acids or arginine at P2; Cathepsin D, active-site aspartic proteases implicated in breast and other cancers, specific for hydrophobic amino acids at P1 and P1'; Cathepsin K, a cysteine protease potentially involved in osteoporosis, whose recognition/cleavage site requires a hydrophobic amino acid at P2. Also acceptable are any of the recognition sequences for the 18 matrix metalloproteases implicated in various aspects of cancer, cell migration and inflamation, including MMP-2 (collagenaseIV), who's optimal substrate is given by the formula: Hyp-Xaa-Pro-Leu-Ala-*-Met-Phe-Gly-Xaa-Hyp. Additional sequences include the thrombin recognition sequence of fibrinogen: Val-Pro-Arg-*-Ser-Phe-Arg; the highly specific D-R-V-Y-I-H-P-F-H-L-*-L-V-Y-S sequence of the renin (an aspartic protease that regulates blood pressure by cleaving and activating angiotensinogen); the C-P-G-R-*-V-V-G-G-S recognition sequence of urokinase (a serine protease and plasminogen activator implicated in cancer); also, tryptases, such as the Gln(Glu)-X-Arg consensus recognition sequence of tryptase Clara (Kido et al. 1999). Tryptases are serine proteases implicated in allergic inflamation and asthma, who's recognition sites are generally characterized by Lys or Arg at P2 and Pro at P3 or P4. Also applicable are recognition sequences for elastases, in particular the serine protease, leukocyte ellastase, which is implicated in pulmonary disease and asthma and who's recognition site is characterized by Leu, Val, Ala, Ser, or Cys at P1. Also applicable are the recognition sites of any of the, predominantly serine-type, proteases involved in coagulation, kinin/kallikrein and complement cascades, as well as those of various cell adhesion molecules (CAMS) (e.g., Hoffman et al. 1998); prostate specific antigen (PSA) (Coombs et al. 1998); and the beta and gamma secretases, implicated in Alzheimer's disease. (Selkoe and Wolfe 2000; Capell et al. 2000; and Sudoh et al. 2000.

Recognition sites for viral and bacterial proteases are also preferred for the practice of the invention. Applicable cleavage sites include, but not limited to the D(E)-X-X-X-X—C(T)-*-S consensus cleavage site of the HCV serine protease, cleavage sites for the Herpesvirus serine protease family, including the consensus cleavage sequence V(L,A)-N(D,Q,E)-A-*-S and recognition sites for Coronavirus and Poliovirus proteases and Rhinovirus 3C cysteine proteases which cleave between Gln and Gly residues. Likewise applicable are the HIV-1 protease cleavage sites such as, for instance, IRKILFLDGI (Christopher et al. Biochemistry 1989, 28(26), 9881–90) and the HSV-1 consensus cleavage site LVLASSSF (O'Boyle et al. 1997).

Also preferred are recognition sites for metalloproteases of *S. macescens, L. pneumophila, P. aeruginosa* and other bacteria characteristic of opportunistic infections. The *P. aeruginosa* cleavage site follows the consensus X-F-*-F(L, Y, V)-A. Also preferred are recognition sequences of the IgA-specific proteases from various pathogenic bacteria such as the *N. gonorrhoeae, N. meningitidis*, and *H. influenzae* serine proteases, and the *S. pneumoniae* and *S. sanguis* metalloproteases, which cleave Pro-Thr and Pro-Ser bonds in the proline-rich hinge regions of IgA. Also applicable is the recognition site for the D-Ala-D-Ala dipeptidase, VanX, a metalloprotease of gram-positive bacteria that destroys a target of vancomycine binding.

Recognition sites for parasite proteases are also preferred, including the malarial plasmepsins—aspartic proteases involved in hemoglobin degradation, which prefer hydrophobic Phe or leu residues at P1 and P1' as well as sites for the *Shistosoma* aspartic and *Leismania* cysteine proteases.

The present invention also relates to the association, or disassociation, of all or a portion of a reporter molecule and a membrane. In one embodiment, the membrane comprises a cell lysate. In another embodiment, the membrane comprises purified or partially purified cellular membranes, for example, nuclear, plasma, mitochondrial, endosomal, or golgi membranes, or vesicles. In another embodiment, the membrane comprises an artificial lipid membrane, such as a vesicle, liposome or lipid mono- or bilayer.

In a preferred embodiment, the membranes are contained within an intact cell. Appropriate cells include prokaryotic and eukaryotic cells, including, but not limited to E. coli, yeast, insect, and mammalian cells. With respect to cells from multicellular animals, an intact cell encompasses both in vivo and ex vivo cells, and thus includes the entire range from immortalized or freshly isolated cultured cells through intact patients.

In a preferred embodiment, the cell is from a patient, hereby defined as any person or non-human animal. Such non-human animals include all domesticated and feral vertebrates, preferably, but not limited to: mice, rats, rabbits, fish, birds, hamsters, dogs, cats, swine, sheep, horses, cattle, and non-human primates. In a highly preferred embodiment, the patient is human.

In another preferred embodiment, the membrane is from or in a tumor cell, preferably a transformed, malignant or cancerous cell, preferably from a patient. The tumor cell may be from a solid or non-solid tumor originating in any cell type or body site including, but not limited to cells derived from cancers of the brain, lung (e.g., small cell and non-small cell), ovary, breast, prostate, skin, and colon, as well as carcinomas and sarcomas. Also preferred are metastatic cells and cells from the site of origin of a tumor. As is recognized by one of skill in the art, in some embodiments it is desirable to obtain a clone of cells, or multiple tumorous cells from the same patient, metastasis, cell mass, or cell line, for use in multiple, repeated, or comparative assays.

Conditions which permit the association of a reporter molecule with a membrane are generally provided by an intact cell or whole cell lysate. Where the localization domain comprises a signal for enzyme-catalysed liplidation, the intact cell or lysate will contain an appropriate lipidating enzyme. Where the membrane comprises a highly purified subcellular membrane component, preferably in an aqueous solution, it may be preferable to supplement the membrane with a lapidating enzyme, for example, by adding a soluble cellular fraction of a cell lysate. Where the localization domain promotes a direct association with a membrane-associated molecule, such as a protein, lipoprotein, glycoprotein, appropriate conditions comprise a membrane containing the appropriate membrane-associated molecule, preferably in an aqueous solution or buffer. Of course, if the localization domain directs an association with lipid components of the membrane, appropriate conditions may comprise an aqueous solution of naturally-derived or synthetic membrane lipids, which may be glycerolipids, phospholipids, sphingolipids, cholesterol, cholines, ethanolamines, myo-inositol, and the like, or combinations thereof.

Conditions which permit the emission of a signal from the detection part depend on the detection system chosen but are, nevertheless, well understood by those of ordinary skill. For example, intrinsically fluorescent proteins are best detected in an aqueous environment, whereas the detection of enzymatic signals (e.g., from alkaline phosphatase, luciferase or beta-galactosidase) may require the addition of exogenous substrates.

Non-limiting examples of reporter molecules that may be used for the present invention are K-Ras-GFP fusion chimers. K-Ras, a small GTP-binding protein targets GFP to the plasma membrane by a C-terminal farnesyl group and a nearby polybasic region. K-Ras-GFP fusion chimer was shown to exist in a dynamic equilibrium that rapidly switches between a plasma membrane bound form and a cytosolic form (Yokoe et al. 1996). GFP had not been commonly used as a co-transfection marker because it leaks out from cells after fixation and permeabilisation with ethanol. To avoid this problem Jiang et al. (1998) fused GFP with the sequence that provides farnesylation and palmitoylation signals for targeting the H-Ras to the plasmamembrane.

Another, non-limiting example of a reporter molecule is EGFP-(DEVD)-RasF, wherein DEVD is a caspase cleavage recognition signal sequence leading to proteolytic cleavage of a detection part from said reporter molecule which can be detected. Of course, in an alternative embodiment, the DEVD recognition signal may be located within the detection domain such that the reporter retains fluorescent characteristics until cleaved by a caspase.

As used herein a localization part comprises one or more localization domains. A localization domain comprises any amino acid sequence which directly or indirectly promotes an association with an artificial or cellular membrane, or a subcellular compartment, which may be soluble. Nevertheless, as used herein, a localization domain is understood to encompass a multiplicity of separable amino acid sequences each of which can directly or indirectly promote association with a membrane or subcellular compartment. In preferred embodiments, localization domains provide means to anchor a detection domain to a membrane. Thus, when incorporated into the reporter molecules described herein, a localization domain preferably comprises at least one anchoring domain, preferably at least one membrane anchoring domain. In preferred embodiments, the membrane anchoring domain comprises one or more signals for enzyme-catalysed lipidation, including but not limited to signals for myristoylation, palmitoylation, and more preferably, geranylgeranylation, or farnesylation, discussed above.

In preferred embodiments the lipidation signal is derived from a ras sequence, preferably, H-, N-, K(i4)A- or K(i4)B-Ras, more preferably, Ki4B-Ras and N-Ras. In one embodiment the lipidation signal sequence comprises a farnesylation signal sequence of a Ras protein or a functional part, derivative and/or analogue thereof. In preferred embodiments, the ras sequence comprises the polylysine region of Ki4B-Ras or N-Ras, including variants thereof. As used herein, a variant comprises a similar amino acid sequence having conservative amino acid substitutions but having essentially the same membrane associative tendency. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. (See Zubay 1983).

Additional acceptable lipidation signals may be derived from portions of GTP-binding proteins and may include peptides encoding the MGC motif of G protein alpha subunits (e.g., alpha subunits of $G_i$, $G_o$, and $G_z$). (Galbiati et al. 1999; Parenti et al. 1993; and Koegl et al. 1994; cAMP-dependent protein kinases, and various retroviral coat proteins. In an intact cell, myristoylation, palmitoylation, geranylgeranylation, and farnesylation signal will tend to promote the preferential associate of a reporter molecule with the inner leaflet of plasma membranes. In contrast, a membrane anchoring domain comprising a signal for the addition of glycosylphosphatidylinositol (GPI) will tend to target the reporter molecule to the outer leaflet of the plasma membrane in an intact cell. (E.g., Seaton et al 2000; and Marcic et al. 2000).

A membrane anchoring domain further comprises sequences which directly associate with a membrane or membrane components. In one embodiment, the membrane anchoring domain is a lipid, steroid, aliphatic, or otherwise lipophilic moiety. In another embodiment, the membrane anchoring domain is a peptide, lipopeptide, or glycopeptide sequence that specifically interacts with a membrane component. In one embodiment, the membrane anchoring domain is a lectin which binds to a carbohydrate moiety of a membrane associated protein. In a preferred embodiment, the membrane anchoring domain comprises a peptide sequence which is specifically recognized by a membrane associated protein. Non-limiting examples include the androgen receptor system described by Georget et al. (1997); protein kinase sequences, including protein kinase C (PKC) sequences, such as that described by Sakai et al (1997); caveolin binding sequences (e.g., Galbiati et al. 1999); plasma membrane G protein-coupled receptors such as parathyroid receptor (Conway et al. 1999); membrane associated viral sequences such as the Nef anchor region. Welker et al. 1998).

In another preferred embodiment, the membrane anchoring domain comprises a polypeptide signal sequence for co-translational or post-translational insertion of a polypeptide directly into a membrane. Such signal sequences are well known in the art and include, γ-factor leader peptide of *Saccharomyces*; the signal sequence for IL-7 described in U.S. Pat. No. 4,965,195; the signal sequence for IL-2 receptor described in Cosman et al. (1984); the IL-4 signal peptide described in EP 367,566; the type I IL-1 receptor signal peptide described in U.S. Pat. No. 4,968,607; and the type H IL-1 receptor signal peptide described in EP 460,846.

Also acceptable are leader sequences for the post-translational insertion into mitochondrial membranes and targeting sequences specific for endoplasmic reticulum, golgi apparatus, peroxisomes nuclear membranes or any other membranous cellular subcompartment.

Alternatively, the reporter molecule may contain a targeting signal for a subcellular compartment, in lieu of a membrane anchor. The targeting signal provides an anchoring domain for maintaining the reporter in a soluble subcellular compartment such as the nucleus. The targeting domain may be from a DNA-binding protein (eg. a transcription factor, helicase, topoisomerase, or polymerase) or DNA-associated protein such as a nucleosomal or nucleolar protein. For example, a small fluorescent protein such as GFP may be fused to $NF_{kappa}B$ via a short linker sequence comprising a caspase 3 cleavage site. When expressed in a cell, the reporter is targeted to the nucleus by the $NF_{kappa}B$ anchor, and may be observed by the expression of a signal from the detection domain. However, upon cleavage at the caspase 3 site, GFP is released from its nuclear anchor and diffuses throughout the cell.

Given that caspases or any protease can be active in the nucleus, one could envision that reporter genes targeted to the nucleus can be "detargeted" by removal of a targeting signal through protease cleavage. Thus, in addition to membrane targeting, reporter gene products can be specifically targeted to other locations by incorporating an anchoring domain for a desired subcellular location. (Chatterjee et al. 1997). Indeed, polypeptides that are destined for the nucleus carry specific targeting signals termed nuclear localization signals (NLS) which catalyze the translocation across the nuclear envelope. Reporter gene products, particularly those of less than about 70 kDa, linked to a NLS by a protease cleavage site are expected to diffuse from the nucleus to the cytoplasm upon protease cleavage. Conversely, reporter gene products, less than about 70 kDa, linked to each other by protease cleavage sites to form a fusion protein of more than 70 kDa are expected to diffuse from the cytosol to the nucleus upon cleavage.

Cleavage of the nuclear enzyme poly-(ADP ribose) polymerase (PARP) is a useful indicator of programmed cell death. It is cleaved from a 116 kD form to 24 kDa and 89 kDa fragments. Caspase-3 and caspase-7 are believed to be primarily responsible for PARP cleavage during apoptosis. (Cohen et al 1997). Thus, in one embodiment, a nuclear anchoring domain may comprise all or a portion of PARP containing an NLS. A fusion protein comprising a GFP detection domain linked by a caspase cleavage site to a PARP (or an NLS from PARP) would localize to the nuclear compartment. Upon cleavage by a caspase, the GFP portion would diffuse from the nucleus, thereby emitting an altered detection signal.

The compositions and methods of the present invention can be applied to one or a multitude of agents, i.e. to one or more agents. As used herein, agents comprise compounds including: chemicals; small molecules such as peptides and nucleic acids; plant, bacterial, fungal, or animal extracts which may contain bioactive molecules; known and suspected carcinogenic agents; inhibitors, ligands, or substrates of enzymes involved in proteolysis, glycosylation, phosphorylation, lipidation, and proteolysis; and known and suspected chemotherapeutic agents, and combinations thereof. Known chemotherapeutic agents include ionizing radiation, cisplatin-transferrin, fluoxetine, staurosporines, vinblastine, methotrexate, 5-fluorouracil, and leucovorin, further examples of which can be found in the Physicians' Desk Reference (2000).

As used herein, agents may further comprise courses of treatment with radiation and/or compounds, including in vitro approximations of courses of treatment in a patient. A course of treatment may take into account such factors as the timing, order, concentration, dose, and method of administering each component of a treatment.

Thus, an agent of the invention may be any bioactive agent, for instance but not limited to a compound such as a molecule, a peptide or a proteinaceous molecule. An agent may also be a virus, phage, prion, prokaryotic or eukaryotic cell, or one or more wavelengths of electromagnetic radiation. Preferably said agent is a compound. Preferably said agent is used in an amount that is not toxic for a normal cell. Preferably said agent is capable of passing the plasma membrane of a cell.

In one embodiment an agent is a proteinaceous molecule. In another embodiment an agent is a proteinaceous molecule encoded by a nucleic acid, wherein the agent is provided to a cell through providing the cell with a nucleic acid encoding the proteinaceous molecule. An agent may act directly on a reporter molecule or indirectly. One possible indirect action is for instance the activation of a signalling route by an agent, wherein the signalling results in a change in the cell resulting in a redistribution of the reporter molecule as indicated by measurement or detection of changes in a signal emitted by the detection part.

As used herein a detection part comprises one or more detection domains. A detection domain is any amino acid sequence, molecule, or portion thereof capable of directly or indirectly generating a detectable signal. As used herein, a detection domain is also understood to encompass a multiplicity of separable amino acid sequences, molecules, or portions thereof, each of which can directly or indirectly generate a detectable signal.

As used herein, a detection part, or domain, may be a resonant, coloured, colourogenic, immunogenic, fluorescent, luminescent, or radioactive probe or moiety. A detection part may also be a proteinaceous molecule which can be detected such as an enzyme like beta-galactosidase, luciferase, alkaline phosphatase, beta-lactamase etc. A detection part may also be any molecule which can be detected with conventional techniques used to tag proteinaceous molecules, including, but not limited to the application of epitope-specific antibodies and the conjugation of small fluorescent molecules. In one embodiment, a detection part encompasses a transcriptional regulator, such as the heterologous reporter system described in U.S. Pat. No. 5,776,675 to Broad.

Preferably a detection domain, is a fluorescent, a radioactive, a luminescent and/or a coloured moiety. Preferably said fluorescent moiety is fluorescent protein, hereby defined as any polypeptide capable of emitting a fluorescent signal detectable above the background fluorescence of an intact cell or membrane composition. Suitable fluorescent proteins include Red Fluorescent Protein (RFP) from species of IndoPacific sea anemone *Discosoma*, Green Fluorescent Protein (GFP) derived from *Aequorea victoria*, and functional parts, derivatives, analogues and/or functionally enhanced versions thereof. A non-limiting example of a functionally enhanced version of GFP is enhanced Green Fluorescent Protein (EGFP) as described in (Yang et al, 1996). RFP, GFP and enhanced versions of GFP (EYFP, EGFP, ECFP, and EBFP) are available from Clonetech. For the purpose of this invention, these polypeptides may be used interchangeably, and may be herein referred to collectively as GFP.

RFP and GFP are intrinsically fluorescent proteins that generate fluorescence without the requirement of any cellular factors making the proteins ideal for studies in live tissue. The most successful application of GFP has been fusion in frame with proteins and subsequent expression in cells to monitor their distribution and fate. GFP has been targeted successfully to practically every major organelle of the cell, including plasma membrane (Tsien 1998). GFP has been targeted to the plasma membrane by fusion to K-Ras (Yokoe et al. 1996), to the last 20 amino acid residues of H-Ras (Jiang et al. 1998), to a pleckstrin homology (PH) domain (Stauffer et al. 1998) or to a glycosylphosphatidylinositol anchor (De Angelis et al. 1998). De Angelis and co-workers discovered that when two GFP molecules are brought into proximity, spectral changes occur which allowed them to define a ratiometric self association index (De Angelis et al. 1998). This aspect may be used to design high throughput screening assays.

Other potential applications of tagged GFP in cytotoxic drug screening are the fusion chimera with a nuclear pore membrane protein (Imreh et al. 1998) or a nuclear RNA helicase (Valdez et al. 1998). The integral nuclear pore membrane protein POM121-GFP fusion is correctly targeted to the nuclear pores in various cell lines, and can be used as a marker for noninvasive studies of nuclear pore distribution and nuclear envelope dynamics. By monitoring the nuclear envelope it is also possible to distinguish between apoptotic and necrotic processes, which can be useful in screening toxic chemicals. The POM121-GFP fluorescence around the nuclear periphery is weaker or missing in apoptotic cells in contrast to the unaffected fluorescence in necrotic cells. Also the drug-induced translocation of the nucleolar RNA helicase/GFP fusion protein from the nucleolus to the nucleoplasm can be useful in determining the efficacy of cytotoxic agents (Valdez et al. 1998). Another GFP-based detection of programmed cell death (apoptosis) was described by Xu et al. (1998).

For the practice of this invention, the absorbance and transfer of energy, with the subsequent emission of a detectable signal, are functionally equivalent to the direct, or indirect emission or production of a signal by a detection domain. And, in one embodiment of the invention, the detection domain may comprise one or more components of a Fluorescence resonance energy transfer (FRET) system. Such aspects may also be used to design high throughput screening assays. FRET is a process in which an excited fluorophore (a resonance donor) transfers its excited state energy to a light absorbing molecule (a resonance acceptor).

In the practice of the present invention, resonance donors and acceptors can be on the same or different molecules. In one embodiment, a reporter molecule comprising a membrane targeting domain, at least one high specificity protease recognition site, and a resonance donor detection domain can comprise a first molecule, The remaining component of the FRET system may then comprise a membrane targeting domain and a resonance acceptor domain. This second molecule may, but does not necessarily, contain a high specificity protease recognition site. Cleavage of the first molecule by the high specificity protease alters the common membrane association of the two molecules, thereby changing the resonance signal. Of course, other combinations of two-part FRET systems are readily apparent to the skilled practitioner. Resonant transfer systems which may be useful in generating and detecting a signal from the detection domain include those described in U.S. Pat. Nos. 5,047,321, 5,340,716, and 5,709,994 to Loken, Ullman, and Pease, respectively.

Resonant transfer can occur between two differently coloured mutants of GFP when brought in close proximity (Mitra et al. 1996). Disruption of the spatial association between the proteins eliminates the FRET effect. For example, when GFP and blue fluorescent protein (BFP), a blue derivative of GFP, are linked by a short peptide containing the caspase-3 recognition sequence DEVD, activation of the intracellular protease caspase-3 during apoptosis can be monitored by the FRET assay. Regarding the key role of caspase-3, monitoring the apoptosis process in live cells is commonly based on the detection of caspase-3 activation, using fluorogenic protease substrates containing the DEVD-recognition sequence.

As disclosed herein, an alteration, or lack of alteration, in the subcellular localization or membrane association of a reporter molecule may be assessed by detecting or determining the signal emitted by one or more detection domains. Detecting refers to the presence or absence of a signal in a particular cell, membrane, or subcellular compartment, e.g., the appearance of a signal where none was previously emitted, or the disappearance of a previously observable signal. Determining encompasses detecting but further entails some measurement of the relative intensity or rate of change of a signal.

As used herein, a localization domain may be any molecule or substance capable of manifesting the distribution of a proteinaceous molecule or other substance in an intact cell, membrane-containing cell lysate, membrane-containing solution, subcellular compartment, or soluble portion of an organelle. Preferably said localization domain is a proteinaceous molecule of a cell or a functional part, derivative and/or analogue thereof.

Said cell may be a prokaryotic cell or a eukaryotic cell. In one embodiment, a reporter molecule within the scope of the invention is generated in, or admixed with a lysate of said cell comprising cellular membranes, which may be purified or enriched according to standard methods. In another embodiment, the reporter molecule is exposed to an artificial lipid membrane, such as a micelle. A non-limiting example of an intact cell is a pathogenic bacterium. A change in the distribution of a pathogenic bacterium encoded proteinaceous molecule may at least in part alter the pathogenicity of said pathogenic bacterium. When said cell is an animal or human cell, it is preferred that said proteinaceous molecule is at least in part involved in a disease of said animal or human.

In one embodiment said cell is a tumour cell, transformed cell, neoplasm, cancer cell, or a derivative thereof such as an established cell line of a tumor or cancer cell. Said cell line may be generated anew from cultured cells or patient cells, or said cell line may be obtained from a tissue collection company. In another embodiment said cell comprises a pathogen, wherein said proteinaceous molecule is a molecule encoded by nucleic acid of said pathogen. A non-limiting example of such a pathogen is a virus. A change in the distribution of a virus encoded proteinaceous molecule may at least in part alter the virulence of said virus. A non-limiting example of a localization domain that may be used in the present invention is the pleckstrin homology (PH) domain (Stauffer et al, 1998). PH domains may be found in a variety of enzymes. They are thought to bind to phosphatidylinositol lipids in membranes. In this way, the PH domain of phospholipase C d1 serves as localization module by binding to phosphatidylinositol 4,5 biphosphate in membranes. A GFP-PH fusion was shown to dissociate from the plasma membrane following receptor stimulation showing that phosphatidylinositol 4,5 biphosphate can have second messenger function (Stauffer et al. 1998). The latter study described a transient dissociation of GFP-PH from the plasma membrane, followed by a rapid redistribution to the plasma membrane (3–8 minutes) which makes this relatively impractical to screen for potential inhibitors of both processes. Preferably but not necessarily, localization domains of the invention redistribute after more than 10 minutes to their original location after providing a cell with an agent of the invention. Most preferably localization domains of the invention do not redistribute significantly to their original location after providing a cell with an agent of the invention.

Distribution may be limited to one or more specific organelles or other discriminatable part in a cell, or cell lysate. However, said distribution may also be a distribution throughout the entire cell or a cytoplasmic distribution.

A localization, or anchoring, domain, preferably a membrane anchoring domain, is a part capable of localising itself and/or a linked molecule, to a certain location in a cell or to a subcellular membrane. A membrane anchoring domain may comprise a proteinaceous part with the intrinsic capacity to localise itself and/or a linked molecule, to a certain location in a cell. Alternatively, a membrane anchoring domain may be a part with the capacity to bind to a different molecule, wherein said different molecule is localized to a certain location in a cell. Furthermore a membrane anchoring domain may also comprise a signal sequence for modifying said localization domain and/or a linked molecule, wherein said modification affects and preferably changes, the distribution of the membrane anchoring domain and/or linked molecule with respect to a cellular membrane. Preferably the signal sequence for modifying the membrane anchoring domain and/or a linked molecule is a signal sequence capable of being recognised by a cellular enzyme machinery for attaching one or more hydrophobic moieties to the membrane anchoring domain and/or linked molecules.

Preferably a hydrophobic moiety of the invention is a fatty acid, an isoprenoid and/or a lipid. Preferably a hydrophobic moiety of the invention is an inositol lipid, preferably a phosphatidylinositol lipid or an glycosyl phosphatidylinositol lipid. Further preferred is a hydrophobic moiety which is a fatty acid, preferably a saturated fatty acid such as stearic, palmitic or myristic acid. Further preferred is a hydrophobic moiety which is an isoprenoid, preferably a 15 carbon ($C_{15}$) isoprenoid farnesyl (F) or a 20 carbon ($C_{20}$) isoprenoid geranylgeranyl (GG). Generally preferred are hydrophobic moiety which comprise isoprene (C5) units and derivatives and/or analogues thereof.

In a preferred embodiment of the invention a membrane anchoring domain comprises a localization domain of a Ras protein. Ras proteins comprise a farnesylation signal sequence which at least in part determines distribution of said Ras proteins to the plasma membrane. Approaches to develop Ras farnesylation inhibitors as potential chemotherapeutic agents for the treatment of Ras related cancer include in vitro and in vivo tests. Based on differences in the affinities of the Ras proteins for farnesyl protein transferase (FPTase), it is particularly important to establish inhibitory activity toward K-Ras, the form of Ras most often mutated in human cancers (Kelloff et al. 1997).

Inhibition of FPTase activity can be determined by measuring the incorporation of tritiated farnesyl pyrophosphate into recombinant Ras proteins or Ras related peptides. For these assays (Reiss et al. 1990, Gibbs et al. 1993, Kohl et al. 1994, James et al. 1995) FPTase was obtained from either purified or (semi) crude extracts of E Coli or mammalian cell lines (Prendergast et al. 1994). The selectivity of inhibitors toward FTase, relative to geranylgeranyl transferases (GG-Tases), can be determined via incorporation of tritiated geranylgeranyl pyrophosphate into appropriate acceptor substrates. Selectivity of FTase inhibitors towards squalene synthase, which catalyses the reductive dimerisation of FPP to form squalene, is typically determined (Cohen et al. 1995).

Inhibition of Ras processing is traditionally done in intact cells over expressing Ras proteins and metabolically labelled with tritiated mevalonate. Metabolites of mevalonic acid, like farnesyl pyrophosphate, are incorporated into proteins (Hancock et al. 1989). Radiolabelled proteins, like Ras can subsequently be immunoprecipitated with specific antibodies (Hancock et al. 1989). Other cellular assays that demonstrate the biological activity of FTase inhibitors (Gibbs et al. 1996) include inhibition of Ras-mediated cellular effects like anchorage independent growth (Kohl et al. 1993, Kohl et al. 1994), reversal (James et al. 1993) of morphological phenotype (e.g. multilayer clumping, Seeburg et al. 1984) and alterations in the cytoskeleton (Prendergast et al. 1994).

The activity of FPT inhibitors on the growth of Ras dependent tumours originating from transformed human (xenograft) or rodent (isograft) cell lines carrying mutant Ras genes can be evaluated in nude mice (Hara et al. 1993). Another in vivo cancer model includes transgenic mice harbouring an activated Ha-Ras gene under control of the mouse mammary tumour virus promotor. These oncomice develop mammary and salivary carcinomas stochastically. In this model, FTase inhibitors cause tumour regression (Kohl et al. 1996). The association of activated Ras genes with oncogenic transformation in experimental animals is well established (Barbacid. 1990). Chemopreventive activity of FTase inhibitors can be tested in chemically induced tumour models related to mutated Ras genes of mouse (Matzinger et al. 1995), rat (Singh et al. 1994) and hamster (van Kranen et al. 1991).

In one embodiment, the invention provides a reporter molecule comprising two or more membrane anchoring domains wherein preferably one comprises a signal sequence for lipid modification of the localization domain and a second comprises a polylysine stretch.

Culturing a cell comprising any reporter molecule of the invention may be performed with any suitable method for culturing said cell provided that the time between providing said agent to said cell and determining the distribution of at least part of said reporter molecule in said cell is sufficiently long to allow detection or determination of a change in the distribution of said reporter molecule.

A change in the distribution of a reporter molecule in a cell as a result of providing the cell with an agent refers in the context of the invention to an observed end result and not to a method in which said result is achieved. For instance, said result may be caused by an actual change in the distribution of said particular reporter molecule from one location in a cell to another location in a cell. Alternatively, an apparent redistribution of a reporter molecule may be caused by a rerouting of newly synthesised, in some cases modified, reporter molecules to a new location in a cell as a result of providing an agent to a cell. In this non-limiting example, reporter molecules synthesised prior to providing a cell with an agent may disappear through turnover of the earlier-synthesized molecules. A change in the distribution of reporter molecules may also be caused by a combination of these processes or via entirely different processes.

The signal or change in the signal from a reporter molecule may provide a marker for a cellular function. Thus, one aspect the invention provides a method for determining the capability of an agent of affecting at least in part a specific function in a cell comprising:

providing a cell or membrane with a reporter molecule comprising a detection part which can be detected and a localization domain capable of determining at least in part the distribution of said reporter molecule in said cell, providing a cell or membrane with said agent, culturing the cell or incubating the membrane and, detecting the distribution of at least the detection part in the cell or membrane.

Similarly, another aspect of the invention provides a method for determining the capability of one or more agents to interfere, at least in part, with the distribution of a proteinaceous molecule in a cell, comprising:

providing a cell or membrane with a reporter molecule comprising a detection part which can be detected and at least one localization domain capable of determining at least in part the distribution of said proteinaceous molecule in said cell;

providing said cell or membrane with said one or more agents, culturing the cell or incubating the membrane and determining the distribution of at least part of said reporter molecule in the cell or membrane.

Preferably, a reporter molecule provided to a cell is effectively only present near the plasma membrane prior to contact with the one or more agents. Preferably the distribution of said reporter molecule is altered through a modification of the localization domain.

In one embodiment said localization domain comprises a lipidation signal sequence, preferably a farnesylation signal sequence. In a preferred embodiment said lipidation signal sequence is a part, derivative and/or analogue of a farnesylation signal sequence of a small GTP-binding protein, preferably a Ras protein, most preferably a c-Ha-ras protein.

A reporter molecule may be provided to a membrane, for instance, through providing an intact cell with a nucleic acid encoding said reporter molecule or alternatively, said reporter molecule may be a proteinaceous molecule encoded by the genome of said cell. Said reporter molecule may also be provided to a cell or membrane solution in the form of a proteinaceous molecule. When a proteinaceous molecule is provided directly to a cell it may, for example, be presented to a cell or membrane as a solution, colloid, or particle capable of being incorporated into a cell by phagocytosis, pinocytosis, electroporation, or fusion with another cell or a membrane vesicle. Where a reporter molecule is provided to a membrane in the absence of an intact cell, said reporter may be transcribed and/or translated in situ, or admixed with the membrane in the form of a proteinaceous molecule.

Thus, a reporter molecule may be provided to a membrane in any vector (vehicle) suitable for introducing said reporter molecule in said membrane. As used herein, a vector comprises any medium, virus, solution, particle, episome, transgene, DNA, or RNA suitable for introducing a reporter molecule to a membrane. For example the reporter molecule may be provided to a membrane in a cell through contacting the cell with the reporter molecule whereafter the reporter molecule enters the cell. However a cell may also be provided with a reporter molecule through a process comprising contacting the cell with a nucleic acid delivery vehicle comprising nucleic acid encoding the reporter molecule. A nucleic acid delivery vehicle may be any type of nucleic acid delivery vehicle including, but not limited, to a calcium phosphate precipate or liposomes. A suitable aqueous solution for electroporating nucleic acid into a cell is in the present invention also regarded as a suitable nucleic acid delivery vehicle. Preferably the nucleic acid delivery vehicle is a virus particle or a functional part, derivative and/or analogue thereof. Preferably the nucleic acid delivery vehicle is an adenovirus particle, an adeno-associated virus particle or a retrovirus particle or a functional part, derivative and/or analogue thereof. In a preferred embodiment the nucleic acid delivery vehicle is a retrovirus particle produced by the stable packaging cell line PT67 LNC-EGFP-(DEVD)-RasF or PT67 LNC-EGFP-RasF.

The cell may be any type of cell of which one wants to be able to change a function in or observe a change in a function. The cell may be a prokaryotic cell or a eukaryotic cell. In one embodiment of the invention the cell is a cancer cell. In another embodiment the cell is suspected of having a low sensitivity for said agent, for example but not limited to a cancer cell suspected of having a low sensitivity for an anti-cancer agent. In one embodiment the cell has a low sensitivity for a first agent, for instance due to the fact that the cell is a drug resistant or multidrug resistant cancer cell, and one or more other agents are added to determine whether the low sensitivity for the first agent can be altered through changing the distribution of a proteinaceous molecule involved in a process causing the low sensitivity of said cell for said first agent.

With the disclosure of this invention, one of ordinary skill may select for agents with the capability of altering the distribution of a reporter molecule in a cell. In a preferred embodiment the invention provides the use of a means and/or a method for a high throughput drug discovery process capable of screening a large number of different agents for their effect on the distribution of a reporter molecule of the invention. As used herein, the term "high throughput" refers to a setting wherein a method of the invention is performed a large number of times in a short timespan, for instance, but not limited to, automation of at least a significant part of said method. In such embodiments, a method of the invention may be performed repeatedly in a relatively short amount of time to assess the capability of a plurality of agents to affect the distribution of a reporter molecule in a cell.

Many variations of high throughput screening are known in the art and applicable to the practice of the present methods. Generally applicable methods include the use of confocal microscopy, the ArrayScan (Cellomics, Pittsburgh, Pa.) high-content screening system (see, Conway et al., 1999), and the autofocusing microscopy techniques of Leblans and Van Donink described in U.S. patent application Ser. No. 09/521,618, filed Mar. 8, 2000.

In one embodiment, the invention provides the use of an agent capable of affecting at least in part the distribution of a substance or a proteinaceous molecule in a cell, for determining whether said agent is capable of altering at least in part a function of said cell. In another embodiment, the invention provides the use of an agent capable of affecting at least in part the distribution of a substance or a proteinaceous molecule in a cell and capable of at least in part altering a function in the cell for the preparation of a medicament.

In one aspect, the invention provides means and methods for the phenotypic characterisation of a cell and a method of measuring a phenotype of a cell. In one embodiment of the invention said cell is a tumor, neoplasm, or cancerous cell. The method may be used to determine the capacity of a cell to respond to a particular agent or treatment. In a preferred embodiment the cell is derived from a patient. Preferably, the method is used to determine the sensitivity of a cell from a patient to a particular agent or type of treatment. Observations regarding the sensitivity of the patient cells can then be used to tailor a treatment schedule to treat the patient for a disease or risk of disease. In one embodiment the phenotype measured may be a drug resistant phenotype, preferably a farnesylation inhibition resistance phenotype. In another embodiment, the phenotype measured is a sensitivity to an agent or treatment. The invention likewise provides a method for measuring a medicinal sensitivity phenotype. Preferably said characterisation involves the determination of the sensitivity of a cell for a particular agent.

In one embodiment of the invention said cell is suspected of having a low sensitivity for said agent, preferably a cancer cell suspected of having a low sensitivity for an anti-cancer agent.

In one aspect the invention provides the use of means and methods of the invention for high throughput drug discovery.

In one embodiment of the invention a cell is provided with a reporter molecule by contacting the cell with a nucleic acid delivery vehicle comprising expressible nucleic acid encoding said reporter molecule and culturing the cell to obtain expression of the reporter molecule. Preferably said nucleic acid delivery vehicle is a virus particle or a functional part, derivative and/or analogue thereof, preferably an adenovirus particle, an adeno-associated virus particle or a retrovirus particle. More preferably said nucleic acid delivery vehicle is a retrovirus particle produced by the stable packaging cell lines PT67 LNC-EGFP-(DEVD)-RasF or PT67 LNC-EGFP-RasF.

In a preferred embodiment, this invention provides a method of assaying for a compound that alters the activity of a high specificity protease comprising:

providing a membrane;
providing a reporter molecule comprising at least one detection domain capable of emitting a signal; at least one high specificity protease recognition site; at least one membrane anchoring domain which promotes the association of the reporter molecule with a membrane; wherein proteolysis of the reporter molecule at said at least one high specificity protease recognition site elicits or alters a signal from the detection domain;
providing conditions which permit the emission of a signal from the detection domain;
detecting or determining the signal emitted by the detection domain;
duplicating the above steps in the presence of a compound to be tested;
comparing the signals emitted in the presence and absence of the compound tested.

In another preferred embodiment, the invention comprises a method for assessing the sensitivity of a cell to a chemotherapeutic agent comprising:

providing a cell to be tested;
expressing a reporter molecule comprising at least one detection domain capable of emitting a signal; at least one high specificity protease recognition site; at least one membrane anchoring domain, which promotes the association of the reporter molecule with a membrane; wherein proteolysis of the reporter molecule at said at least one high specificity protease recognition site elicits or alters a signal from the detection domain in the cell;
detecting or determining the signal emitted by the detection domain;
duplicating the above steps in the presence of a chemotherapeutic agent to be tested;
comparing the signals emitted in the presence and absence of the agent tested.

Yet another preferred embodiment comprises a method for selecting a chemotherapeutic therapy comprising:

providing a multiplicity of malignant cells from a patient;
introducing into the cells, a reporter molecule comprising at least one detection domain capable of emitting a signal; at least one high specificity protease recognition site; at least one membrane anchoring domain which promotes the association of the reporter molecule with a membrane; wherein proteolysis of the reporter molecule at said at least one high specificity protease recognition site elicits or alters a signal from the detection domain;
assessing the sensitivity by detecting or determining the signal emitted by the detection domain in the presence and absence of at least one chemotherapeutic agent; and
selecting an appropriate chemotherapeutic therapy for treating the patient.

In another aspect of the invention, a reporter molecule is introduced into a cell by exposing the cell to a vector comprising a nucleic acid capable of directing the expression of said reporter molecule In another aspect the invention provides a reporter molecule comprising a detection part and a localization domain, further comprising a linking part which links said detection part and said localization domain. Preferably said linking part comprises a specifically cleavable amino acid sequence, preferably a high specificity protease recognition sequence. Preferably said amino acid sequence is capable of being cleaved by a caspase. Preferably said localization domain comprises a localization domain of RasF or a functional part, derivative and/or analogue thereof. Preferably said detection part comprises an intrinsically fluorescent protein, such as enhanced green fluorescent protein or a functional part, derivative and/or analogue thereof. More preferably said reporter molecule is Enhanced Green Fluorescent Protein-(DEVD)-RasF or a functional part, derivative and/or analogue thereof.

In one embodiment the invention provides an Enhanced Green Fluorescent Protein-RasF or a functional part, derivative and/or analogue thereof.

In another embodiment the invention provides a cell comprising a reporter molecule according to the invention. In a preferred embodiment, the reporter molecule is expressed in the cell.

In yet another embodiment the invention provides a nucleic acid encoding a reporter molecule of the invention, or a functional part, derivative and/or analogue thereof.

In still another embodiment the invention provides a nucleic acid delivery vehicle, or vector, comprising a nucleic acid encoding a reporter molecule of the invention, or a functional part, derivative and/or analogue thereof.

plasma membrane. We fused the C-terminal membrane targeting signal sequence of the human c-Ha-ras1 (J00277, NCBI) to the C-terminal end of EGFP (Clontech).

Farnesylation Assay

Twenty amino acids of the C-terminal end of c-Ha-ras 1 located in exon 4 were added to the C-terminus of the EGFP coding sequence by polymerase chain reaction (PCR) cloning.

The PCR amplification of EGFP was done with a 3' (antisense) primer (SEQ ID NO 1 and SEQ ID NO 2) which contains the following regions shown below in sense: (i) the codons of the 6 C-terminal amino acid residues of EGFP, (ii) followed downstream by codons corresponding to 20 C-terminal amino acid residues of c-Ha-ras1 (iii) in turn followed by a Hind 111 cut (adapter) site, (iiii) ending with an irrelevant tctgtc sequence which is believed to facilitate Hind III digestion. Note that by this PCR the multiple cloning site of pEGFP-C1 was deleted and the stop codon (*) of c-Ha-ras1 is included.

```
5' ATG GAG GAG CTG TAC AAG AAG CTG AAC CCT CCT GAT GAG AGT GCC
    M   D   E   L   Y   K   K   L   N   P   P   D   E   S   G
    <        EGFP           ><        Ras plasmamembrane CCC GGC TGC ATG AGC TGC AAG TGT GTG CTC TCC TGA AAG CTT tct gtc 3'
 P   G   C   M   S   C   K   C   V   L   S   *
targeting signal sequence                        ><Hind III>
```

In one aspect the invention provides the use of a localization domain of a cellular proteinaceous molecule in a reporter molecule, for selecting an agent capable of at least in part affecting distribution of said proteinaceous molecule in a cell comprising said proteinaceous molecule, from a group of agents.

With the term "lipidation signal sequence" as used herein is meant a signal sequence as a result of which a molecule is provided with one or more lipid moieties.

The antisense oligonucleotide used in the PCR reaction was 5'GACAGAAAGCTTTCAGGAGAGCACA-CACTTGCAGCTCATGCAGCCGGGGCCACT CTCAT-CAGG AGGGTTCAGCTTCTTGTACAGCTCGTCCAT 3'. (SEQ ID NO: 3)

Caspase Assay

For the apoptosis construct, the same primer was used except that a sequence encoding DEVD (i.e. caspase 3 and 7 cleavage site) was included between EGFP and the Ras plasmamembrane targeting signal sequence (SEQ ID NO 4 and SEQ ID NO 5).

```
5' ATG GAC GAG CTG TAC AAG GAC GAG GTG GAC AAG CTG AAC CCT CCT
    M   D   E   L   Y   K   D   E   V   D   K   L   N   P   P
    <        EGFP           ><   caspase   ><   Ras plasmamembrane GAT GAG AGT GGC CCC GGC TGC ATG AGC TGC AAG TGT GTG CTC TCC TGA AAG CTT tct gtc 3'
 D   E   S   G   P   G   C   M   S   C   K   C   V   L   S   *
targeting signal sequence                                ><Hind III>
```

The present invention is illustrated by the following Examples, which are merely exemplary and not intended to be limiting in any way.

EXAMPLES

Constructs and Cell Lines

The idea was to target EGFP to the plasma membrane by using a farnesylation signal sequence. The CAAX motif appears to be the sole recognition site for the enzyme farnesyl transferase; hence, addition of CAAX sequences to ectopic proteins renders them substrates for farnesylation. The last 20 amino acids of c-Ha-Ras provides farnesylation and palmitoylation for targeting the Ras protein to the The antisense oligonucleotide used in the PCR reaction was: 5'GACAGAAAGCTTTCAGGAG AGCACACACT-TGCAGCTCATGCAGCCGGGGCCACTCT-CATCAGGAGGGTTCAGCTT GTCCACCTCGTCCTTG-TACAGCTCGTCCAT 3' (SEQ ID NO:6)

The same 5' (sense) primer was used in the farnesylation assay and in the caspase assay. In this primer, shown below, a Kozak sequence is incorporated because pLNCX, the expression vector for the EGFP-(DEVD)-farnesyl, does not contain a Kozak sequence. This sequence is believed to improve translation. 5' to 3', the primer contains (i) an irrelevant gacaga sequence flanking the Hind III site, believed to facilitate Hind III digestion (ii) a region matching the Kozak sequence (underlined) and (iii) 15 nucleotides of EGFP coding sequence corresponding to the 5 N-terminal amino acid residues overlapping the Kozak sequence. The sense oligonucleotide in the PCR reaction was identical to this given below.

(SEQ ID NO: 7)
5' ga cag aAA GCT T<u>TCGCCACCATG</u> GTG AGC AAG GGC 3'
        <Hind III><   Kozak     >
                         <     EGFP     >

The PCR yielded fragments designated EGFP-(DEVD)-RasF which was cloned in the Hind III site of the retroviral vector pLNCX. The resulting construct, pLNC-EGFP-(DEVD)RasF was confirmed by sequence analysis. pLNCX, derived from Moloney murine leukemia virus (Mo-MuLV), is designed for retroviral gene delivery and expression (Miller and Rosman, 1989). This vector contains a neomycin resistance (N) gene controlled by 5' viral LTR (L) for antibiotic selection in eukaryotic cells and a cloning site X (Hind III, HpaI and ClaI) downstream from a cytomegalovirus (C) immediate early promotor. The y sequence is an extended viral packaging signal required for the viral vector transcript to be packaged in virions. pLNCX does not contain the viral structural genes (gag-pol and env) necessary for particle formation and replication. However, they can be provided in trans in packaging cell lines stably expressing these genes. One such commercially available cell line, PT67, expresses the gag-pol and env genes from two separate plasmids. The env (envelope) gene which determines viral tropism allows viral particles formed by PT67 cells to infect a wide variety of target cell types. After infection, reverse transcription and stable chromosomal integration of the viral vector occurs in the target cell. When the target cells do not contain complementary viral genes, the retroviral vector, containing the gene(s) of interest remains integrated in the form of a replication incompetent provirus.

The amphotropic packaging cell line PT67 (Clontech) was transfected (Pfx-2, Invitrogen) with pLNC-EGFP-(DEVD)-RasF and selected in 400 µg/ml G418. In the surviving colonies, transcription occurs from (a) stably integrated plasmid(s) pLNC-EGFP-(DEVD)RasF. The resulting LNC-EGFP-(DEVD)-RasF mRNA is translated into EGFP-(DEVD)-RasF and the neomycin resistance protein and is also packaged into replication incompetent virions. Thus, the PT67-pLNC-EGFP-(DEVD)-RasF constitutively produces viral particles, able to transmit the EGFP-(DEVD)-RasF and the neomycin resistance gene at the same time. These amphotropic virions give the flexibility to rapidly develop novel cell lines stably expressing EGFP-(DEVD)-RasF proteins. In this way, the K562 and MT4 (suspension) cell lines were co-cultured for 96 h with virus producing (adherent) PT67-pLNC-EGFP-RasF and PT67-pLNC-EGFP-(DEVD)-RasF cells, respectively. Gene transfer referred to as transduction in K562 and MT4 cells was easily observed by fluorescence microscopy.

K562 (MT4) cells were separated from PT67-pLNC-EGFP-(DEVD)-RasF and Non transduced K562 (MT4) cells were removed by selection in 400 µg/ml G418. The remaining fluorescent K562 (MT4) cells were directly cloned in 96 well plates by fluorescence activated cell sorting using an automatic cell deposit unit. Gating was set in such a way that only highly fluorescent cells were deposited in wells containing 50 µl of 100% foetal calf serum. After 1 h. 200 µl RPMI medium (+10% fetal calf serum) containing G418, taking into account a final concentration of 400 µg/ml, was added. Two weeks later, appropriate clones were selected by visual inspection using a fluorescence microscope and designated K562-LNC-EGFP-RasF or MT4-LNC-EGFP-(DEVD)-RasF. The same transduction scheme can in principle be applied to any cell line of interest. When the target cell line is adherent like the producer on can imagine co-culture without physical contact.

Farnesyl Transferase Inhibition Assay

Figure 1B:
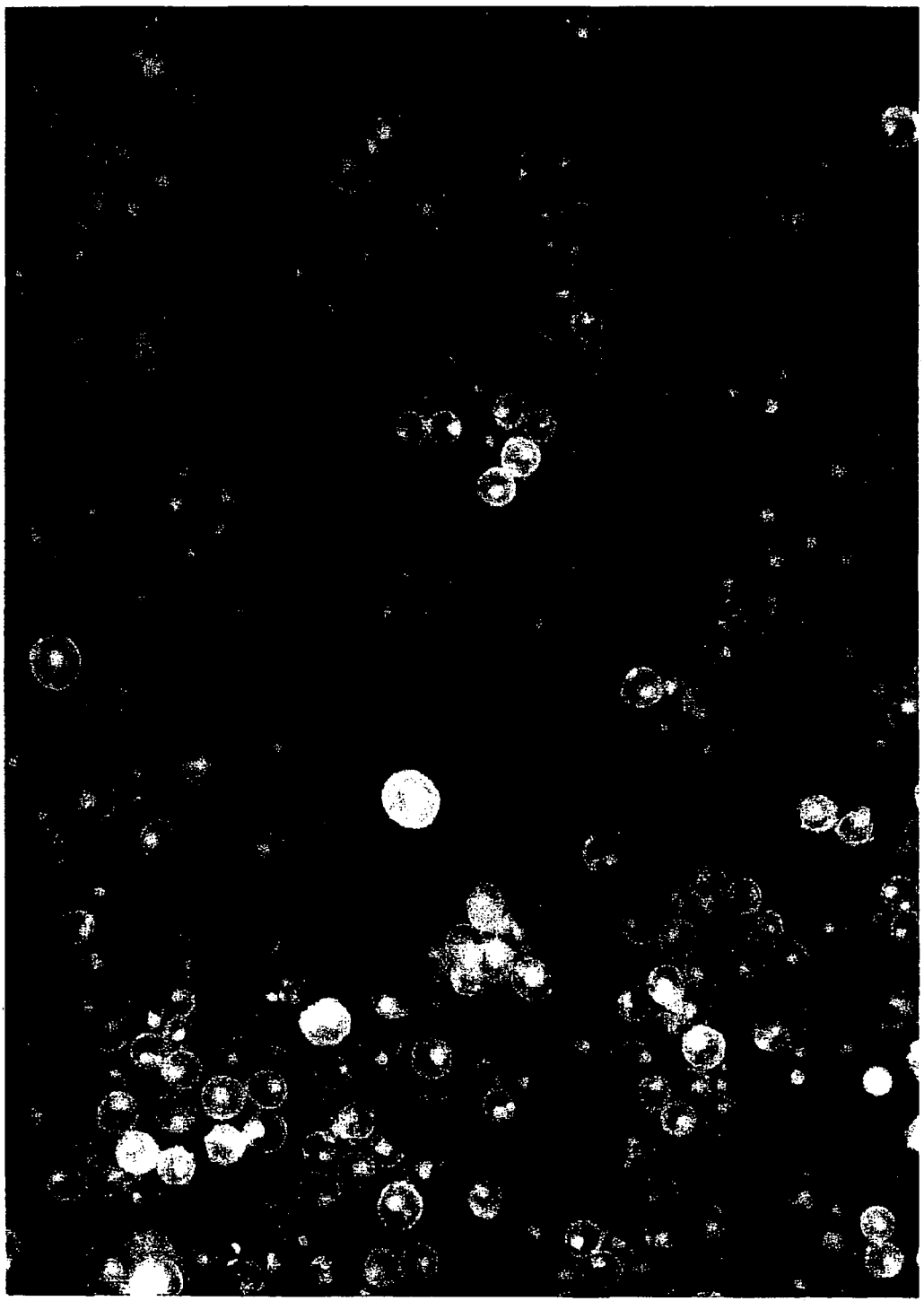

If EGFP-RasF is substrate for farnesyl transferase and hence is farnesylated, we expect to observe EGFP's fluorescence to be seen at the plasma membrane level. Close microscopic examination of K562 cells (FIG. 1, magnification 240× (A) and 480× (B)) clearly shows that this is indeed the case. Thus, delineation of the plasma membrane indicates that EGFP modification with a membrane targeting signal caused EGFP to relocalise to the plasma membrane. In cells expressing EGFP without a farnesylation signal sequence, fluorescence is observed throughout the cell. Regarding the bright spots in the cells we speculate that this represents EGFP targeted around the Golgi apparatus.

Figure 2A:
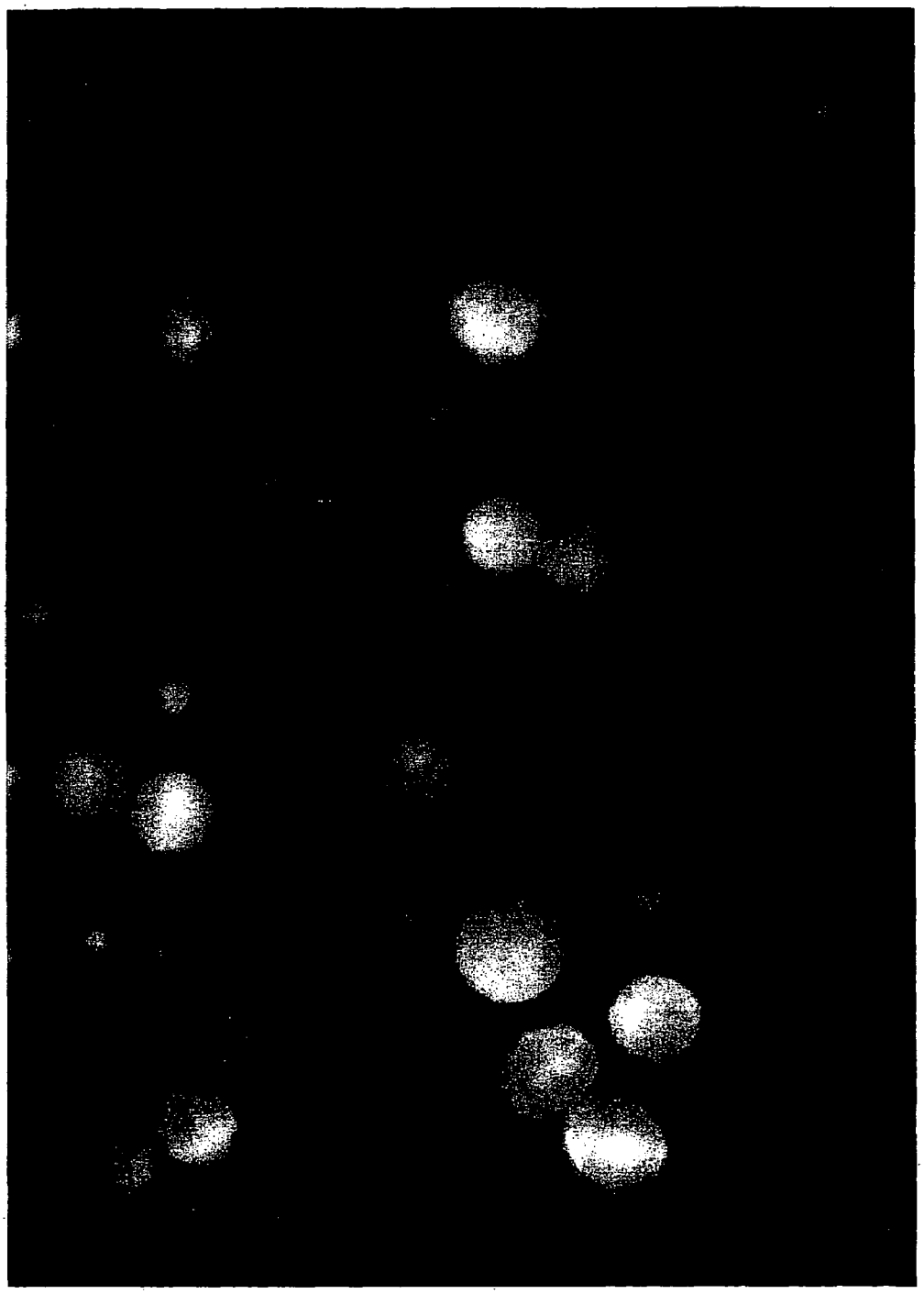
FIG. 2. Addition of the well known farnesyl transferase inhibitor, FTI-276 (5 µM) to K562 LNC-EGFP-RasF cells at low (A, 240×) and high (B, 480×) magnification. Inhibition of farnesylation results in disruption of membrane localization.
Figure 2B:
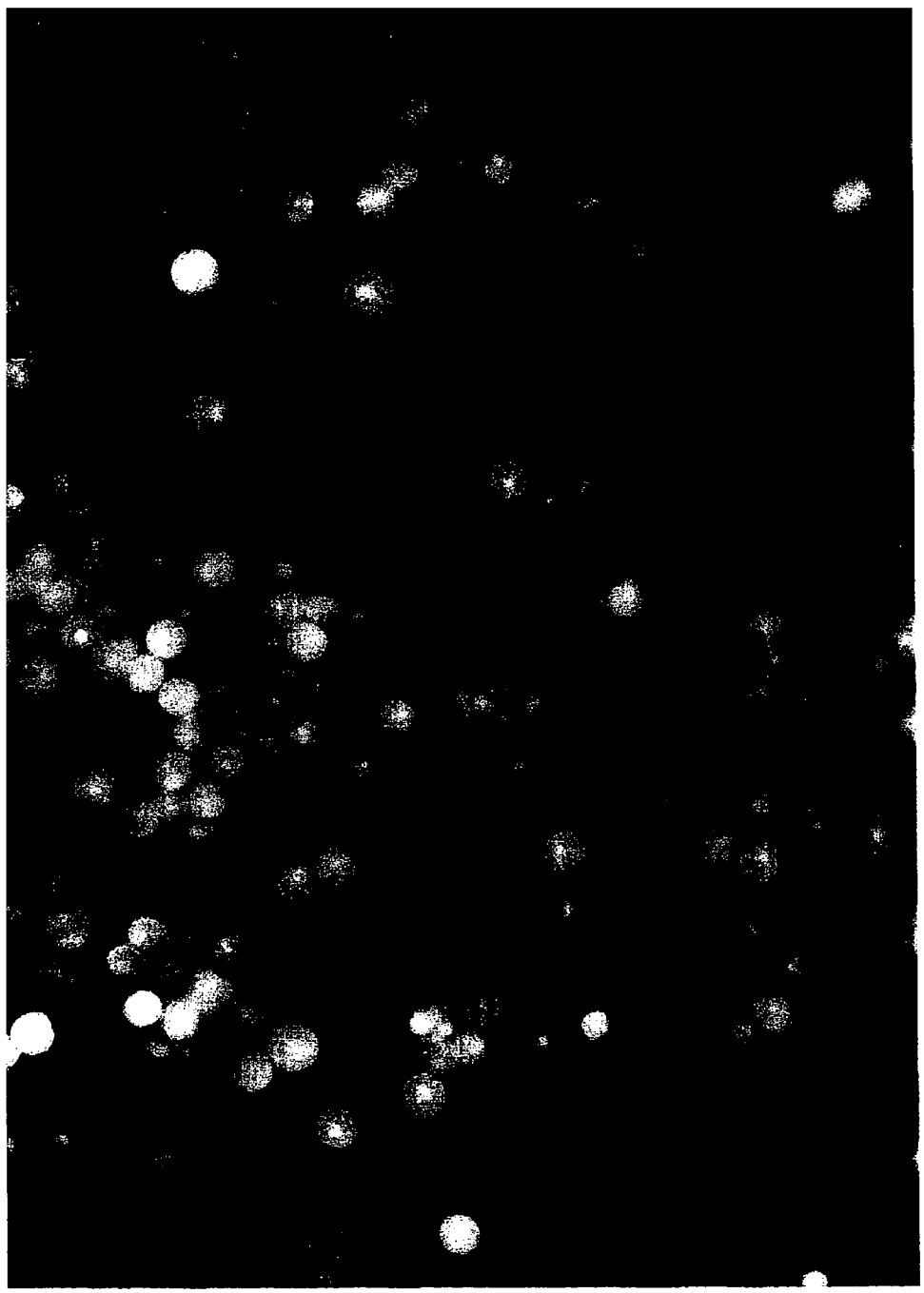

Disruption of farnesylation and consequently of membrane distribution should be monitored in these cells upon exposure to farnesyl transferase inhibitors. The effect of the well known Farnesyl transferase inhibitor FTI-276 (Calbiochem) is shown in FIG. 2 (magnification 240× (A) and 480× (B)). At high enough concentrations (>5 µM) the EGFP compartmentalisation almost completely disappears upon addition of the inhibitor. Farnesyl transferase inhibition apparently results in detachment of EGFP-(DEVD)-RasF from the inner leaflet of the plasma membrane and evenly distributes throughout the cell. This translocation of EGFP is striking enough for us to assume that (digital) imaging and appropriate image analysis should allow us to quantitate this process. In view of the fact that Ras proteins require post translation modification with a farnesyl moiety for oncogenic activity and that farnesyl transferase inhibitors are considered to have potential as anti-cancer agents this cellular assay is very well suited to the discovery of novel drugs that specifically interfere with farnesylation.

Caspase Assay

Figure 3A:
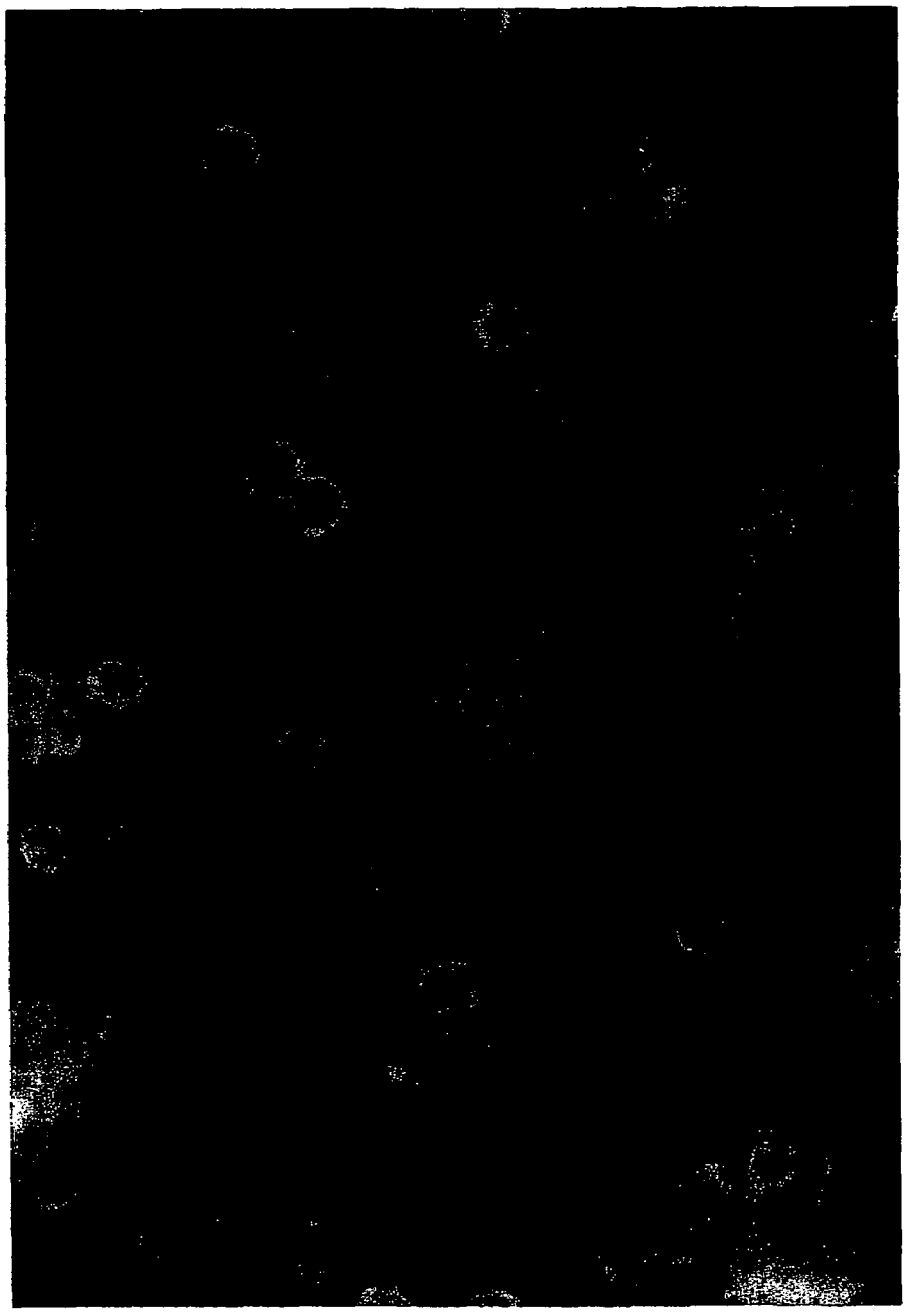
FIG. 3. MT4-LNC-EFGP-DEVD-RasF cells (A) express membrane targeted EGFP. DEVD is a recognition site for caspases 3 and 7, key enzymes involved in apoptosis, and is located between the farnesylation signal sequence and EGFP. Cleavage of this linker sequence by caspases after exposure to the apoptosis inducer staurosporin indicates apoptosis. (B) Induction of apoptosis (10 μM staurosporin, 4 h) in MT4-LNC-EFGP-DEVD-RasF cells is apparent by reduced EGFP membrane targeting.
Figure 3B:

Incorporation of a caspase recognition site (DEVD) between the EGFP C-terminus and the farnesylation signal sequence also results in targeting to the plasmamembrane of MT4 cells (FIG. 3 A). The DEVD sequence does apparently not impair farnesylation. Cleavage of the DEVD pentapeptide by caspase 3 and/or caspase 7 is an established indication of apoptosis. MT4 cells were chosen because we were previously able to show staurosporine induced caspase 3 activity in these cells using the fluorogenic Ac(N-acetyl)-DEVD-AMC substrate (Pharmingen, results not shown). After exposure of MT4-LNC-EGFP-DEVD-RasF cells to 10 µM staurosporin for 4 hours, membrane targeting of EGFP partially disappears (FIG. 3 B) as inferred from the uniform fluorescence distribution in the cells.

Figure 4A:
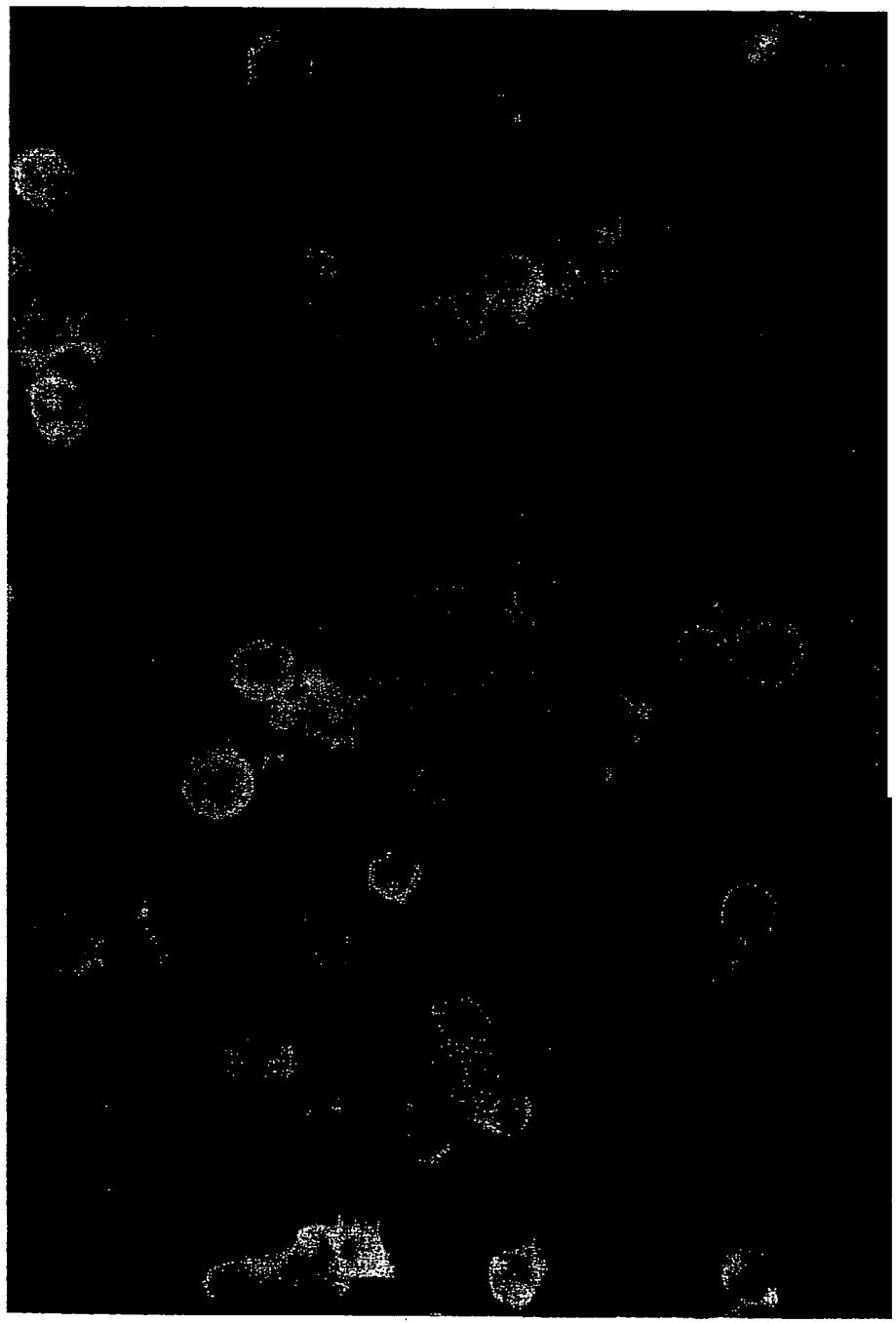
FIG. 4. (A) MT4-LNC-EFGP-RasF cells also express EGFP at membrane height. The protein does not contain DEVD between the farnesylation signal sequence and EGFP. (B) Induction of apoptosis by staurosporin (4 h) altered cell morphology but did not result in marked translocation of EGFP compared to FIG. 3B.
Figure 4B:

This observation can be explained when assuming caspase 3/7 cleavage at the DEVD site thereby breaking the link between EGFP and the membrane targeting signal. If EGFP translocation is caused by the well known apoptosis inducer staurosporin, we do not expect this phenomenon to occur in MT4-LNC-EGFP-RasF cells lacking the DEVD cleavage site. FIG. 4 B shows that this is indeed the case. In this figure it is seen that although staurosporin affects the cells morphology within hours as deduced from the more round up shape compared to irregular shaped cells in FIG. 4 A (no staurosporin added) no prominent translocation of EGFP occurs. The only difference between MT4-LNC-EGFP-RasF and MT4-LNC-EGFP-DEVD-RasF is the presence or not of the DEVD cleavage site, indicating DEVD and hence caspase 3/7 activity is involved in the detachment of EGFP from the plasma membrane.

CITED LITERATURE

Each of the following is specifically incorporated herein in its entirety: Aoyama et al. J Med Chem. 1998, 41: 143–147./Armstrong et al. J Biol. Chem. 1995, 270: 7864–7868./Barbacid Annu Rev Biochem. 1987, 56: 779–827./Barbacid Eur J Clin Invest. 1990, 20: 225–235./Bellamy Br. Med. Bul 1996, 53: 522–538./Bishop et al. J Biol. Chem. 1995, 270: 30611–30618./Bos Cancer Res. 1989, 49: 4682–4689./Bos Mutat Res. 1988, 195: 255–271./Capell et al. (2000) J Biol. Chem. 2000 May 8 (published electronically as manuscript MO-03202). (PMID: 10801872 UI)./Casey et al. Proc Natl Acad Sci USA. 1989, 86: 8323–8327./Cescato et al., J. Neurochem. 2000 March; 74(3):1131–9./Chatterjee et al. U Exp Cell Res. 1997 Oct. 10; 236(1):346–50./Clarke S Annu Rev Biochem. 1992, 61: 355–386./Cohen Biochem. J. 1997. 326:1–16./Cohen et al. Biochem. Pharmacol. 1995, 49: 839–845./Conway et al. (1999) J. Biomolec. Screen. 4:75/Coombs et al. (1998) Chem Biol. 5(9):475–88./Cosman et al. Nature 312:768 (1984)./Cox et al. J Biol. Chem. 1994, 269: 19203–19206./De Angelis et al. Proc. Natl. Acad. Sci. USA. 1998, 95: 12312–12316./EP 367,566./Galbiati et al. (1999) J. Biol. Chem. 274:5843. Georget et al. (1997) Mol. Cel. Endocrin. 129:17./Gibbs et al. J. Biol. Chem. 1993, 268: 7617–7620./Gibbs et al. Breast Cancer Res Treat. 1996, 38: 75–83./Gibbs et al. Cell. 1994, 77: 175–178./Glomset et al. Trends Biochem. Sci. 1990, 15: 139–142./Gurtu V et al. 1997. ClonTech Application Notes Vol XII, no3./Hamstra et al. (1999) Hum. Gene. Ther. 10(2):235./Hancock J F et al. Cell. 1989, 57: 1167–1177./"Handbook of Proteolytic Enzymes," A. J. Barrett, N. D. Rawlings & J. F. Woessner Eds. (Academic Press, London 1998)./Hancock J F et al. Cell. 1990, 63: 133–139. Hara M et al. Proc. Natl. Acad. Sci. USA. 1993, 90: 2281–2285. Hill C S et al. Cell. 1995, 80: 199–211./Hoffman et al. (1998) Brain Res 811(1–2):152. Imreh G et al. Exp. Cell Res. 1998, 238:371–376./Jackson J H et al. Proc Natl Acad Sci USA. 1990, 87: 3042–3046./James GL et al. Methods Enzymol. 1995a, 255:38–60./James G L et al. Science. 1993, 260:1 937–942./James G L et al. J Biol. Chem. 1994, 269: 27705–27714./James G L et al. J Biol. Chem. 1995b, 270: 6221–6226./James G L et al. J Biol. Chem. 1994, 269: 14182–14190./Jiang W et al. Biotechniques. 1198, 24: 348–354./Karin M et al. Curr Biol. 1995, 5: 747–757./Kato K et al Proc Natl Acad Sci USA. 1992, 89: 6403–6407./Kelloff G J et al. Cancer Epidemiol Biomarkers Prev. 1997, 6: 267–282./Khosravi-Far R et al. J Biol. Chem. 1992, 267: 24363–24368./Khosravi-Far R et al. Cancer Metastasis Rev. 1994, 13: 67–89./Kido et al. (1999) Mol Cells 9:235/Koegl et al. (1994) Biochem. J. 303, 749/Kohl N E et al. Science. 1993, 260: 1934–1937/Kohl N E et al. Nat. Med. 1995, 1: 792–797./Kohl N E et al. Proc. Natl. Acad. Sci. USA. 1994, 91: 9141–9145./Lerner E C et al. J Biol. Chem. 1995, 270: 26802–26806./Lerner E C et al. J Biol. Chem. 1995b, 270: 26770–26773./Lowy et al. Annu Rev Biochem 1993, 62: 851–891./Maltese W A FASEB J., 1990, 4: 3319–3328./Maltese et al. J Cell Physiol. 1987, 133: 471–481./Marcic et al. (2000) J. Biol. Chem. 2000 275(21):16110–16118./Matzinger et al Carcinogenesis. 1995, 16: 2487–2492./McIlhinney R A. Trends Biochem Sci 1990 October; 15(10):387–391/Miller et al Biotechniques 1989 (9):980–2, 984–6, 989–90./Miyake M et al. FEBS Lett. 1996, 378: 15–18./Moomaw et al. J Biol. Chem. 1992, 267: 17438–17443./Moores et al. J Biol. Chem. 1991, 266: 14603–14610./Nicholson et al (1999) Cell Death and Differentiation 6:1028–42/O'boyle et al. (1997) Virology 236 (2):338–47/Omer et al. Trends Pharmacol Sci. 1997, 18: 437–444./Parenti et al. (1993) Biochem. J. 291:349/Physicians' Desk Reference (2000)/Prendergast et al Mol. Cell. Biol. 1994, 14: 4193–4202./Prendergast G C et al Cancer Res. 1996, 56: 2626–2632./Pronk et al. Biochim Biophys Acta. 1994, 1198: 131–147./Reiss et al. Cell. 1990, 62: 81–88./Reiss et al. Proc Natl Acad Sci USA. 1991, 88: 732–736./Rowell C A, et al. J Biol. Chem. 1997, 272: 14093–14097./Sakai et al., (1997) J. Cell Biol. 139:1465/Sambrook et al. *Molecular Cloning: A Laboratory Manual*, Vols. 1–3, (2d ed. 1989), Cold Spring Harbor Laboratory Press./Schafer et al Science. 1989, 245: 379–385./Schafer et al. Annu Rev Genet. 1992, 26: 209–237./Schmidt Biochim. Biophys. Acta. 1989, 988: 411–426./Seabra et al. J Biol. Chem. 1992, 267: 14497–14503./Seaton et al. (2000) Biol. Reprod. 62(6):1667–1676./Sebti et al. Pharmacol Ther. 1997, 74: 103–14./Seeburg et al. Nature. 1984, 312: 71–75./Selkoe and Wolfe, (2000) Proc Natl Acad Sci USA. 97(11): 5690–5692./Sepp-Lorenzino L, et al. FEBS Lett. 1989, 245: 110–116./Shaham et al. Genes Dev. 1996, 10:578–591./Shirasawa et al. Science. 1993, 260: 85–88./Singh et al. Carcinogenesis. 1994, 15: 1317–1323./Sinn E., et al. Cell. 1987, 49: 465–475./Smets Anticancer drugs 1994, 5:3–9./Stacey et al. Mol Cell Biol. 1991, 11: 4053–4064./Stauffer T. P., et al. Current Biology. 1998, 8: 343–346./Stennicke et al. (1999) Cell Death and Differentiation 6:1054–59/Stroh et al., Death by a thousand cuts: an ever increasing list of caspase substrates, (1998) 5:997–1000./Sudoh et al., (2000) Eur J Biochem. 267(7):2036–45./Sun et al Oncogene. 1998, 16: 1467–1473./Thornberry N A, et al., Science 1998, 281: 1312–1316./Thornberry, N A et al., J. Biol. Chem. 1997, 272: 17907–17911./Tsien Annu Rev Biochem. 1998, 67: 509–544./U.S. patent application Ser. No. 09/521,618, filed Mar. 8, 2000. (Leblans and Van Donink)/U.S. Pat. No. 4,965,195./U.S. Pat. No. 4,968,607./U.S. Pat. No. 5,047,321/U.S. Pat. No. 5,340,716/U.S. Pat. No. 5,709,994./U.S. Pat. No. 5,776,675/Valdez et al., Biotechniques 1998, 24: 1032–1036./van Kranen Carcinogenesis. 1991, 12: 1477–1482./Wang et al. J. Cell. Physiol 1997, 173: 247–255./Weidemann et al. (1999) J. Biol. Chem. (1999) 274(9):5823/Weinberg et al. Sci AM 1996, 275:62–70/Welker et al, (1998) J. Virol. 72:8833/Whyte et al. J Biol. Chem. 1997, 272: 14459–14464./Wilcox C, et al. Science 1987 238: 1275–1278./Wildmann et al. J. Biol. Chem. 1998, 273: 7141–7147./Willumsen et al. Nature. 1984, 310: 583–586./Xu et al, Nucl. Acids. Res. 1998, 26:2034–2035./Yang et al. Nucl. Acids Res. 1996, 24(22), 4592–4593./Yokoyama et al. J Biol. Chem. 1993, 268: 4055–4060./Yokoyama et al. Proc Natl Acad Sci USA. 1991, 88: 5302–5306./Zhang et al. Annu Rev Biochem. 1996, 65: 241–269./Zubay, *Biochemistry*, Addison-Wesley Pub. Co., (1983).

We claim:

1. A method for identifying a test agent that redistributes a membrane anchor and/or a reporter molecule comprising:
   A) providing a reporter molecule comprising:
      a) at least one detection domain capable of emitting a fluorescent, luminescent, or chromatic signal or capable of absorbing a resonant frequency;
      b) at least one membrane anchoring domain comprising an amino acid sequence capable of promoting lipidation, wherein the at least one membrane anchoring domain comprises signals for myristoylation wherein the reporter molecule is provided by a nucleic acid vector;
   B) providing a cell to be tested, wherein said cell contains a lipidating enzyme wherein the reporter molecule enters the cell;
   C) providing a lipid source for lipidation;
   D) providing conditions which permit the reporter molecule to associate with cellular membranes of the cell to be tested;
   E) providing conditions which permit the emission of the signal from the detection domain;
   F) observing or measuring the signal emitted by the detection domain;
   G) duplicating steps A) through E) in the presence of the agent to be tested; and
   H) comparing the signals emitted in the presence and absence of the agent tested, wherein the redistribution of the membrane anchor, and/or reporter molecule is assessed.

2. The method of claim 1 wherein the membrane anchoring domain comprises at least one member selected from: 1) an amino acid sequence for palmitoylation; 2) the polylysine region of KiB-Ras; and 3) the c-Ha-ras plasma membrane targeting signal sequence.

3. The method of claim 1 wherein the detection domain comprises a fluorescent protein.

4. The method of claim 3 wherein the nucleic acid vector comprises, a retroviral vector, or an adenoviral vector.

5. The method of claim 1 wherein the fluorescent protein is green fluorescent protein, red fluorescent protein or enhanced versions of green fluorescent protein.

6. The method of claim 1 wherein the nucleic acid vector is contained in a liposome or an electroporation medium.

* * * * *

SEQUENCE LISTING

<160> NUMBER OF SEQ ID NOS: 38

<210> SEQ ID NO 1
<211> LENGTH: 93
<212> TYPE: DNA
<213> ORGANISM: Artificial Sequence
<220> FEATURE:
<223> OTHER INFORMATION: Primer

<400> SEQUENCE: 1

```
atggacgagc tgtacaagaa gctgaaccct cctgatgaga gtggccccgg ctgcatgagc      60
tgcaagtgtg tgctctcctg aaagctttct gtc                                   93
```

<210> SEQ ID NO 2
<211> LENGTH: 26
<212> TYPE: PRT
<213> ORGANISM: Artificial Sequence
<220> FEATURE:
<223> OTHER INFORMATION: Primer

<400> SEQUENCE: 2

```
Met Asp Glu Leu Tyr Lys Lys Leu Asn Pro Pro Asp Glu Ser Gly Pro
1               5                   10                  15

Gly Cys Met Ser Cys Lys Cys Val Leu Ser
            20                  25
```

<210> SEQ ID NO 3
<211> LENGTH: 93
<212> TYPE: DNA
<213> ORGANISM: Artificial Sequence
<220> FEATURE:
<223> OTHER INFORMATION: Oligonucleotide

<400> SEQUENCE: 3

```
gacagaaagc tttcaggaga gcacacactt gcagctcatg cagccggggc cactctcatc      60
aggagggttc agcttcttgt acagctcgtc cat                                   93
```

<210> SEQ ID NO 4
<211> LENGTH: 105
<212> TYPE: DNA
<213> ORGANISM: Artificial Sequence
<220> FEATURE:
<223> OTHER INFORMATION: Synthetic Construct

<400> SEQUENCE: 4

```
atggacgagc tgtacaagga cgaggtggac aagctgaacc ctcctgatga gagtggcccc      60
ggctgcatga gctgcaagtg tgtgctctcc tgaaagcttt ctgtc                      105
```

<210> SEQ ID NO 5
<211> LENGTH: 30
<212> TYPE: PRT
<213> ORGANISM: Artificial Sequence
<220> FEATURE:
<223> OTHER INFORMATION: Synthetic Construct

<400> SEQUENCE: 5

```
Met Asp Glu Leu Tyr Lys Asp Glu Val Asp Lys Leu Asn Pro Pro Asp
1               5                   10                  15

Glu Ser Gly Pro Gly Cys Met Ser Cys Lys Cys Val Leu Ser
            20                  25                  30
```

```
<210> SEQ ID NO 6
<211> LENGTH: 105
<212> TYPE: DNA
<213> ORGANISM: Artificial Sequence
<220> FEATURE:
<223> OTHER INFORMATION: Oligonucleotide

<400> SEQUENCE: 6
gacagaaagc tttcaggaga gcacacactt gcagctcatg cagccggggc cactctcatc     60
aggagggttc agcttgtcca cctcgtcctt gtacagctcg tccat                    105

<210> SEQ ID NO 7
<211> LENGTH: 35
<212> TYPE: DNA
<213> ORGANISM: Artificial Sequence
<220> FEATURE:
<223> OTHER INFORMATION: Oligonucleotide

<400> SEQUENCE: 7
gacagaaagc tttcgccacc atggtgagca agggc                                35

<210> SEQ ID NO 8
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 8

Cys Ala Ala Xaa
1

<210> SEQ ID NO 9
<211> LENGTH: 4
<212> TYPE: PRT
<213> ORGANISM: Artificial Sequence
<220> FEATURE:
<223> OTHER INFORMATION: Synthetic Construct

<400> SEQUENCE: 9

Gly Gly Pro Pro
1

<210> SEQ ID NO 10
<211> LENGTH: 4
<212> TYPE: PRT
<213> ORGANISM: Artificial Sequence
<220> FEATURE:
<223> OTHER INFORMATION: Synthetic Construct

<400> SEQUENCE: 10

Cys Ala Ala Leu
1

<210> SEQ ID NO 11
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: Xaa can be any naturally occurring amino acid
```

```
<400> SEQUENCE: 11

Xaa Xaa Cys Cys
1

<210> SEQ ID NO 12
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 12

Xaa Cys Xaa Cys
1

<210> SEQ ID NO 13
<211> LENGTH: 4
<212> TYPE: PRT
<213> ORGANISM: Artificial Sequence
<220> FEATURE:
<223> OTHER INFORMATION: Synthetic Construct

<400> SEQUENCE: 13

Pro Ala Arg Pro
1

<210> SEQ ID NO 14
<211> LENGTH: 4
<212> TYPE: PRT
<213> ORGANISM: Artificial Sequence
<220> FEATURE:
<223> OTHER INFORMATION: Synthetic Construct

<400> SEQUENCE: 14

Asp Glu Val Asp
1

<210> SEQ ID NO 15
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 15

Asp Xaa Xaa Asp
1

<210> SEQ ID NO 16
<211> LENGTH: 5
<212> TYPE: PRT
<213> ORGANISM: Artificial Sequence
<220> FEATURE:
<223> OTHER INFORMATION: Synthetic Construct

<400> SEQUENCE: 16
```

```
Tyr Val His Asp Ala
1               5
```

<210> SEQ ID NO 17
<211> LENGTH: 4
<212> TYPE: PRT
<213> ORGANISM: Artificial Sequence
<220> FEATURE:
<223> OTHER INFORMATION: Synthetic Construct

<400> SEQUENCE: 17

```
Glu Gly Phe Pro
1
```

<210> SEQ ID NO 18
<211> LENGTH: 4
<212> TYPE: PRT
<213> ORGANISM: Artificial Sequence
<220> FEATURE:
<223> OTHER INFORMATION: Synthetic Construct

<400> SEQUENCE: 18

```
Trp Glu His Asp
1
```

<210> SEQ ID NO 19
<211> LENGTH: 4
<212> TYPE: PRT
<213> ORGANISM: Artificial Sequence
<220> FEATURE:
<223> OTHER INFORMATION: Synthetic Construct

<400> SEQUENCE: 19

```
Asp Glu His Asp
1
```

<210> SEQ ID NO 20
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Trp or Leu

<400> SEQUENCE: 20

```
Xaa Glu Gly Asp
1
```

<210> SEQ ID NO 21
<211> LENGTH: 4
<212> TYPE: PRT
<213> ORGANISM: Artificial Sequence
<220> FEATURE:
<223> OTHER INFORMATION: Synthetic Construct

<400> SEQUENCE: 21

```
Val Glu His Asp
1
```

<210> SEQ ID NO 22
<211> LENGTH: 4
<212> TYPE: PRT
<213> ORGANISM: Artificial Sequence
<220> FEATURE:

```
<223> OTHER INFORMATION: Synthetic Construct

<400> SEQUENCE: 22

Leu Glu Thr Asp
1

<210> SEQ ID NO 23
<211> LENGTH: 4
<212> TYPE: PRT
<213> ORGANISM: Artificial Sequence
<220> FEATURE:
<223> OTHER INFORMATION: Synthetic Construct

<400> SEQUENCE: 23

Ile Glu Thr Asp
1

<210> SEQ ID NO 24
<211> LENGTH: 4
<212> TYPE: PRT
<213> ORGANISM: Artificial Sequence
<220> FEATURE:
<223> OTHER INFORMATION: Synthetic Construct

<400> SEQUENCE: 24

Leu Glu His Asp
1

<210> SEQ ID NO 25
<211> LENGTH: 4
<212> TYPE: PRT
<213> ORGANISM: Artificial Sequence
<220> FEATURE:
<223> OTHER INFORMATION: Synthetic Construct

<400> SEQUENCE: 25

Ile Glu Pro Asp
1

<210> SEQ ID NO 26
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Hyp
<220> FEATURE:
<221> NAME/KEY: MISC_FEATURE
<222> LOCATION: (8)..(8)
<223> OTHER INFORMATION: Xaa = Hyp

<400> SEQUENCE: 26

Xaa Pro Leu Ala Met Phe Gly Xaa
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Construct

<400> SEQUENCE: 27

Val Pro Arg Ser Phe Arg
1               5
```

```
<210> SEQ ID NO 28
<211> LENGTH: 14
<212> TYPE: PRT
<213> ORGANISM: Artificial Sequence
<220> FEATURE:
<223> OTHER INFORMATION: Synthetic Construct

<400> SEQUENCE: 28

Asp Arg Val Tyr Ile His Pro Phe His Leu Leu Val Tyr Ser
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Synthetic Construct

<400> SEQUENCE: 29

Cys Pro Gly Arg Val Val Gly Gly Ser
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Asp or Glu
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa = Cys or Thr

<400> SEQUENCE: 30

Xaa Xaa Xaa Xaa Xaa Xaa Ser
1               5

<210> SEQ ID NO 31
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Val or Leu or Ala
<220> FEATURE:
<221> NAME/KEY: MISC_FEATURE
<222> LOCATION: (2)..(2)
<223> OTHER INFORMATION: Xaa = Asn or Asp or Gln or Glu

<400> SEQUENCE: 31

Xaa Xaa Ala Ser
1

<210> SEQ ID NO 32
<211> LENGTH: 10
<212> TYPE: PRT
<213> ORGANISM: Artificial Sequence
<220> FEATURE:
```

<223> OTHER INFORMATION: Synthetic Construct

<400> SEQUENCE: 32

Ile Arg Lys Ile Leu Phe Leu Asp Gly Ile
1               5                   10

<210> SEQ ID NO 33
<211> LENGTH: 8
<212> TYPE: PRT
<213> ORGANISM: Artificial Sequence
<220> FEATURE:
<223> OTHER INFORMATION: Synthetic Construct

<400> SEQUENCE: 33

Leu Val Leu Ala Ser Ser Ser Phe
1               5

<210> SEQ ID NO 34
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa = Phe or Leu or Tyr or Val

<400> SEQUENCE: 34

Xaa Phe Xaa Ala
1

<210> SEQ ID NO 35
<211> LENGTH: 4
<212> TYPE: PRT
<213> ORGANISM: Artificial Sequence
<220> FEATURE:
<223> OTHER INFORMATION: Synthetic Construct

<400> SEQUENCE: 35

Asp Ala Asp Ala
1

<210> SEQ ID NO 36
<211> LENGTH: 4
<212> TYPE: PRT
<213> ORGANISM: Artificial Sequence
<220> FEATURE:
<223> OTHER INFORMATION: Synthetic Construct

<400> SEQUENCE: 36

Glu Tyr Phe Pro
1

<210> SEQ ID NO 37
<211> LENGTH: 4
<212> TYPE: PRT
<213> ORGANISM: Artificial Sequence
<220> FEATURE:
<223> OTHER INFORMATION: Synthetic Construct

<400> SEQUENCE: 37

Glu Cys Phe Pro
1

```
<210> SEQ ID NO 38
<211> LENGTH: 4
<212> TYPE: PRT
<213> ORGANISM: Artificial Sequence
<220> FEATURE:
<223> OTHER INFORMATION: Synthetic Construct

<400> SEQUENCE: 38

Glu Asx Phe Pro
1
```